(12) United States Patent
Yamazaki et al.

(10) Patent No.: US 12,715,825 B2
(45) Date of Patent: Aug. 25, 2026

(54) DATA PROCESSING DEVICE AND GAS CONVERSION SYSTEM

(71) Applicant: KABUSHIKI KAISHA TOSHIBA, Tokyo (JP)

(72) Inventors: Hiroaki Yamazaki, Yokohama Kanagawa (JP); Ping Wang, Fujisawa Kanagawa (JP); Ryota Kitagawa, Tokyo (JP)

(73) Assignee: KABUSHIKI KAISHA TOSHIBA, Kawasaki Kanagawa (JP)

(*) Notice: Subject to any disclaimer, the term of this patent is extended or adjusted under 35 U.S.C. 154(b) by 723 days.

(21) Appl. No.: 18/171,941

(22) Filed: Feb. 21, 2023

(65) Prior Publication Data

US 2024/0083826 A1 Mar. 14, 2024

(30) Foreign Application Priority Data

Sep. 14, 2022 (JP) ................................ 2022-146134

(51) Int. Cl.
*C07C 1/12* (2006.01)
*C01B 3/06* (2026.01)
(Continued)

(52) U.S. Cl.
CPC .................. *C07C 1/12* (2013.01); *C01B 3/06* (2013.01); *C01B 13/0207* (2013.01);
(Continued)

(58) Field of Classification Search
None
See application file for complete search history.

(56) References Cited

U.S. PATENT DOCUMENTS

2008/0202028 A1 8/2008 Tsangaris et al.
2018/0164137 A1* 6/2018 Layher .................. G01F 1/6965
2021/0079542 A1 3/2021 Kitagawa et al.

FOREIGN PATENT DOCUMENTS

EP 3540428 A1 * 9/2019 ......... G01N 33/0009
JP H4-294215 A 10/1992
(Continued)

OTHER PUBLICATIONS

Japan Patent Office, Office Action in JP App. No. 2022-146134 (May 2, 2025).

*Primary Examiner* — Matthew G Marini
(74) *Attorney, Agent, or Firm* — Finnegan, Henderson, Farabow, Garrett & Dunner, LLP

(57) ABSTRACT

According to one embodiment, a data processing device includes an acquisitor and a processor. The acquisitor can acquire a first concentration signal obtained from a first concentration sensor configured to detect a first concentration of a first target substance included in a first output gas and a first flow rate signal obtained from a first flow rate sensor configured to detect a first flow rate of the first output gas. The processor can derive a first concentration value corresponding to the first concentration based on the first concentration signal. The processor can derive a first corrected conversion coefficient obtained by correcting a first conversion coefficient regarding a relationship between the first flow rate signal and the first flow rate based on the first concentration value. The processor can derive a first flow rate value corresponding to the first flow rate based on the first flow rate signal.

7 Claims, 18 Drawing Sheets

(51) Int. Cl.
*C01B 13/02* (2006.01)
*C01B 32/40* (2017.01)
*G01F 1/74* (2006.01)
*G01N 33/00* (2006.01)

(52) U.S. Cl.
CPC ................ *C01B 32/40* (2017.08); *G01F 1/74* (2013.01); *G01N 33/0067* (2013.01)

(56) References Cited

FOREIGN PATENT DOCUMENTS

| | | | |
|---|---|---|---|
| JP | H5-99724 | A | 4/1993 |
| JP | 2008-545840 | A | 12/2008 |
| JP | 2016-85131 | A | 5/2016 |
| JP | 2021-46574 | | 3/2021 |
| WO | WO 2022/010967 | A1 | 1/2022 |

* cited by examiner

DATA PROCESSING DEVICE AND GAS CONVERSION SYSTEM

CROSS-REFERENCE TO RELATED APPLICATIONS

This application is based upon and claims the benefit of priority from Japanese Patent Application No. 2022-146134, filed on Sep. 14, 2022; the entire contents of which are incorporated herein by reference.

FIELD

Embodiments described herein relate generally to a data processing device and a gas conversion system.

BACKGROUND

For example, there is a gas conversion system that converts carbon dioxide into another gas for use. Accurate detection of the resulting gas is required in a gas conversion system.

DETAILED DESCRIPTION

Figure 1:
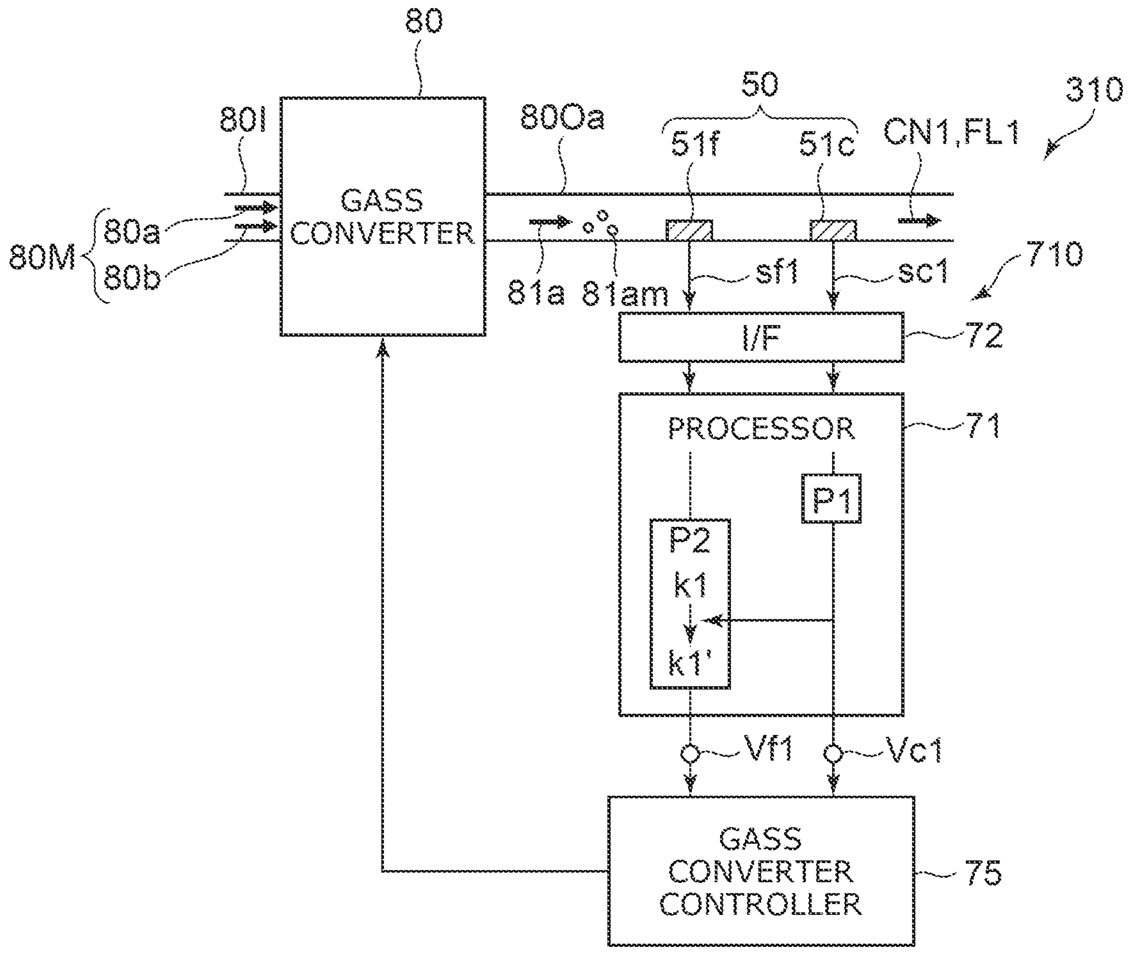
FIG. 1 is a schematic view illustrating a data processing device and a gas conversion system according to a first embodiment.

According to one embodiment, a data processing device includes an acquisitor and a processor. The acquisitor is configured to acquire a first concentration signal obtained from a first concentration sensor configured to detect a first concentration of a first target substance included in a first output gas and a first flow rate signal obtained from a first flow rate sensor configured to detect a first flow rate of the first output gas. The processor is configured to derive a first concentration value corresponding to the first concentration based on the first concentration signal. The processor is configured to derive a first corrected conversion coefficient obtained by correcting a first conversion coefficient regarding a relationship between the first flow rate signal and the first flow rate based on the first concentration value. The processor is configured to derive a first flow rate value corresponding to the first flow rate based on the first flow rate signal using the first corrected conversion coefficient.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic view illustrating a data processing device and a gas conversion system according to a first embodiment.

As shown in FIG. 1, a data processing device 710 according to the embodiment includes an acquisitor 72 and a processor 71. The acquisitor 72 can obtain a first concentration signal sc1 and a first flow rate signal sf1. The acquisitor 72 is, for example, an interface.

For example, a first concentration sensor 51*c* is provided. The first concentration sensor 51*c* can detect a first concentration CN1 of a first target substance 81*am* included in a first output gas 81*a*. A first flow rate sensor 51*f* can detect a first flow rate FL1 of the first output gas 81*a*. The acquisitor 72 acquires the first concentration signal sc1 obtained from the first concentration sensor 51*c* and the first flow rate signal sf1 obtained from the first flow rate sensor 51*f*. The first concentration sensor 51*c* and the first flow rate sensor 51*f* are included in a sensor device 50, for example.

The processor 71 acquires these signals from the acquisitor 72. The processor 71 can derive a first concentration value Vc1 corresponding to the first concentration CN1 based on the first concentration signal sc1. For example, the processor 71 derives the first concentration value Vc1 by performing a first process P1 based on the first concentration signal sc1.

On the other hand, the processor 71 performs a second process P2. In the second process P2, the processor 71 derives a first flow rate value Vf1 corresponding to the first flow rate FL1 based on the first flow rate signal sf1. At this time, a conversion coefficient "k" relating to the relationship between the first flow rate signal sf1 and the first flow rate value Vf1 is used. A conversion coefficient "k" is, for example, a conversion factor. In the embodiment, the conversion coefficient "k" is corrected by the first concentration value Vc1. "Flow rate" is, for example, a volume of gas flowing per unit time.

For example, the processor 71 can derive a first corrected conversion coefficient k1' obtained by correcting the first conversion coefficient k1 relating to the relationship between the first flow rate signal sf1 and the first flow rate FL1 based on the first concentration value Vc1. The processor 71 can derive the first flow rate value Vf1 corresponding to the first flow rate FL1 based on the first flow rate signal sf1 using the first corrected conversion coefficient k1'.

In the first flow rate sensor 51*f*, the first flow rate signal sf1 is output as a detection value of the first flow rate FL1 of the first output gas 81*a*. In the second process P2, the value of the first flow rate signal sf1 is calculated as the first flow rate value Vf1 using the conversion coefficient "k". At this time, the first flow rate signal sf1 output from the first flow rate sensor 51*f* not only changes according to the first flow rate FL1, but also the concentration of the first target substance 81*am* included in the first output gas 81*a* (and the type of substance). This is based on the fact that the characteristics of the first output gas 81*a* change depending on the concentration of the first target substance 81*am* (and the type of substance). The characteristics of the first output gas 81*a* include, for example, specific heat, thermal conductivity, or specific gravity or the like.

Therefore, the conversion coefficient "k" depends on the concentration of the first target substance 81*am* (and the type of substance) and is not necessarily constant.

In the embodiment, the first corrected conversion coefficient k1' obtained by correcting the first conversion coefficient k1 based on the first concentration value Vc1 is used. By deriving the first flow rate value Vf1 based on the first flow rate signal sf1 using the first corrected conversion coefficient k1', the flow rate can be detected more accurately. According to the embodiment, it is possible to provide a data processing device capable of improving characteristics.

As described above, in the embodiment, the detection result of the first flow rate sensor 51*f* is corrected using the detection result of the first concentration sensor 51*c* to calculate the flow rate. Therefore, the time delay in detection by the first concentration sensor 51*c* is small. For example, the absolute value of the difference between the time at which the acquisitor 72 obtains the first concentration signal sc1 from the first concentration sensor 51*c* and the time at which the acquisitor 72 obtains the first flow rate signal sf1 from the first flow rate sensor 51*f* is 10 seconds or less. Smaller time differences allow for more accurate correction.

For example, there is a reference example in which detection by a concentration sensor takes a long time. For example, in the concentration sensor, a concentration is detected by a chromatograph. In such a reference example, if the flow rate fluctuates during detection by the concentration sensor, the concentration detected by the concentration sensor cannot follow the fluctuating flow rate. For this reason, in the reference example, the concentration detection result is not used to correct the conversion coefficient relating to the flow rate.

On the other hand, in the embodiment, the conversion coefficient used for calculating the flow rate is corrected using the short-time detection result of the first concentration sensor 51*c*. This allows accurate flow rate detection.

In embodiments, at least a part of the first concentration sensor 51*c* has a MEMS structure. Thereby, the concentration can be detected in a short time. An example of the configuration of the first concentration sensor 51*c* will be described later.

As shown in FIG. 1, the first output gas 81*a* is output from a gas converter 80. For example, the gas converter 80 includes an input part 80I and a first output part 80Oa. These may be, for example, pipes. A first substance 80*a* is introduced into the input part 80I. In one example, the first substance 80*a* includes, for example, carbon dioxide. In this example, a second substance 80*b* is also introduced into the input part 80I. The second substance 80*b* includes hydrogen, for example. The first substance 80*a* and the second substance 80*b* are included in an input gas 80M.

The gas converter 80 can convert at least a part of the input gas 80M including the first substance 80*a* into the first output gas 81*a*. For example, the following chemical reactions occur.

$$CO_2+4H_2\text{->}CH_4+2H_2O$$

This chemical reaction yields the first output gas 81*a*. In this case, the first output gas 81*a* includes at least one selected from the group consisting of methane, water, carbon dioxide and hydrogen. Thus, in one example, the first output gas 81*a* includes at least one selected from the group consisting of methane, water, carbon dioxide and hydrogen.

The output gas flow rate and concentration (and type) can be detected with high accuracy. The product of flow rate, concentration and time allows more accurate detection of the amount of material converted.

As shown in FIG. 1, a gas conversion system 310 according to the embodiment includes the data processing device 710, the first concentration sensor 51*c*, the first flow rate sensor 51*f*, and the gas converter 80. The place where the data processing device 710 is installed may be different from the place where the first concentration sensor 51*c*, the first flow rate sensor 51*f* and the gas converter 80 are installed. Signals (or information) may be sent and received in any manner, wired or wireless.

As shown in FIG. 1, the gas conversion system 310 may further include a gas converter controller 75. The gas converter controller 75 can control the gas converter 80 based on at least one of the first concentration value Vc1 or the first flow rate value Vf1 derived by the processor 71. The gas converter 80 can be operated more efficiently.

Figure 2:
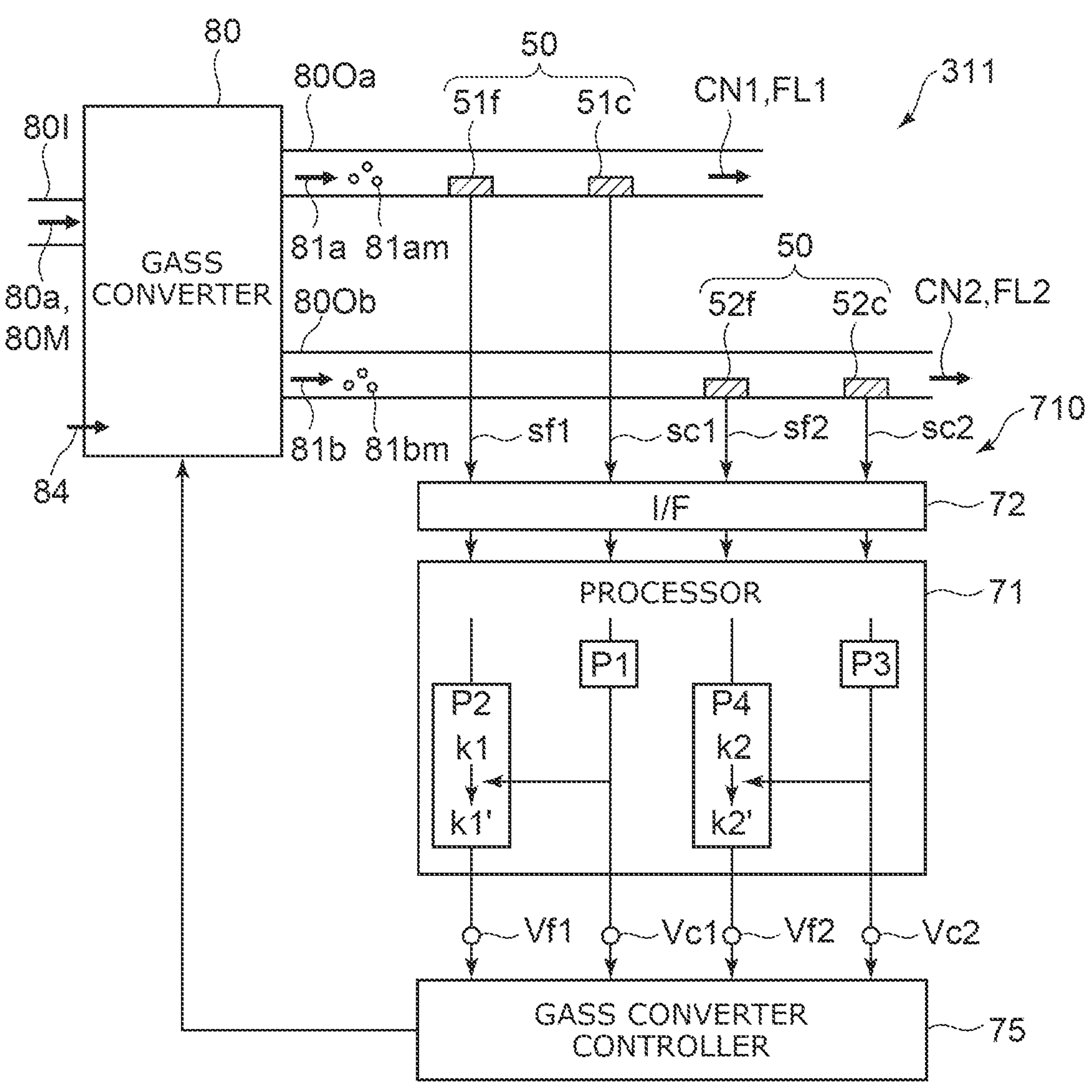
FIG. 2 is a schematic view illustrating a data processing device and a gas conversion system according to the first embodiment.

FIG. 2 is a schematic view illustrating a data processing device and a gas conversion system according to the first embodiment.

As shown in FIG. 2, in this example, the acquisitor 72 can obtain the first concentration signal sc1, the first flow rate signal sf1, a second concentration signal sc2 and a second flow rate signal sf2.

For example, the gas converter 80 outputs a second output gas 81*b* in addition to the first output gas 81*a*. Detection of the first output gas 81*a* is performed in the same manner as in the example of FIG. 1. The detection of the second output gas 81*b* will be described below.

The acquisitor 72 can further acquire the second concentration signal sc2 and the second flow rate signal sf2. The second concentration signal sc2 is obtained from the second concentration sensor 52*c* capable of detecting a second concentration CN2 of a second target substance 81*bm* included in the second output gas 81*b*. The second flow rate signal sf2 is obtained from a second flow rate sensor 52*f* capable of detecting a second flow rate FL2 of the second output gas 81*b*.

The processor 71 can derive a second concentration value Vc2 corresponding to the second concentration CN2 based on the second concentration signal sc2. For example, the second concentration value Vc2 is derived by a third process P3.

The processor 71 can derive a second corrected conversion coefficient k2' obtained by correcting a second conversion coefficient k2 regarding the relationship between the second flow rate signal sf2 and the second flow rate FL2 based on the second concentration value Vc2. The processor 71 can derive the second flow rate value Vf2 corresponding to the second flow rate FL2 based on the second flow rate signal sf2 using the second corrected conversion coefficient k2'. For example, in a fourth process P4, derivation (correction) of the second corrected conversion coefficient k2' and derivation of the second flow rate value Vf2 are performed.

For example, the flow rate and concentration can be detected with high accuracy for each of multiple types of output gases (first output gas 81*a* and second output gas 81*b*).

In the example of FIG. 2, the absolute difference between the time at which the acquisitor 72 obtains the second concentration signal sc2 from the second concentration sensor 52*c* and the time at which the acquisitor 72 obtains the second flow rate signal sf2 from the second flow rate sensor 52*f* is preferably 10 seconds or less. The absolute value of the difference may be 5 seconds or less. The absolute value of the difference may be 2 seconds or less.

At least a part of the second concentration sensor 52*c* preferably has a MEMS structure. Thereby, the concentration can be detected in a short time.

The second output gas 81*b* is output from the gas converter 80. The gas converter 80 can convert at least a part of the input gas 80M including the first substance 80*a* into the first output gas 81*a* and the second output gas 81*b*. The first output gas 81*a* is output from the first output part 80Oa. The second output gas 81*b* is output from a second output part 80Ob. In this example, the gas converter 80 includes an electrolytic solution 84.

In one example, the gas converter 80 can use the electrolytic solution 84 to generate the first output gas 81*a* and the second output gas 81*b* from the first substance 80*a*. For example, the first substance 80*a* includes carbon dioxide. Heat and electric power can be supplied to the gas converter 80 from the outside. A catalyst may be placed within the gas converter 80 to allow the conversion reaction to occur.

For example, the following chemical reaction occurs. The chemical reaction may include an electrochemical reaction.

$$CO_2+H_2O\text{->}CO+H_2+O_2$$

For example, carbon monoxide, hydrogen and oxygen are obtained from the first substance 80*a* (carbon dioxide) and water. For example, the first output gas 81*a* includes at least one selected from the group consisting of carbon monoxide, hydrogen, water and carbon dioxide. The second output gas 81*b* includes at least one selected from the group consisting of carbon dioxide, oxygen, hydrogen and water. The flow rates and concentrations (and types) of multiple output gases including multiple types of target substances (first target substance 81*am* and second target substance 81*bm*) can be detected with high accuracy. The product of flow rate, concentration and time allows more accurate detection of the amount of material converted.

In the example of FIG. 2 as well, the detection value may be supplied to the gas converter controller 75. The gas converter controller 75 can control the gas converter 80 based on at least one of the first concentration value Vc1, the first flow rate value Vf1, the second concentration value Vc2, and the second flow rate value Vf2. The gas converter 80 can be operated more efficiently.

FIGS. 3A to 3D are schematic views illustrating a part of the gas conversion system according to the embodiment.

Figure 3A:
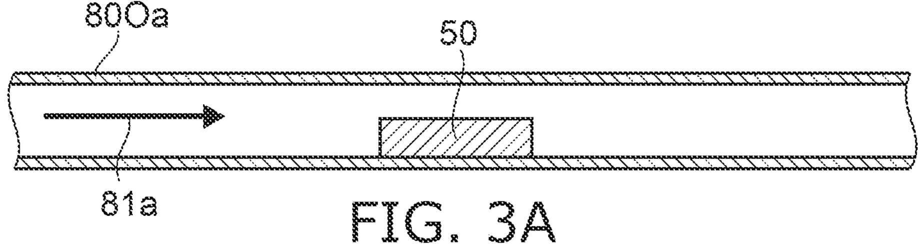
FIGS. 3A to 3D are schematic views illustrating a part of the gas conversion system according to the embodiment.
Figure 3B:
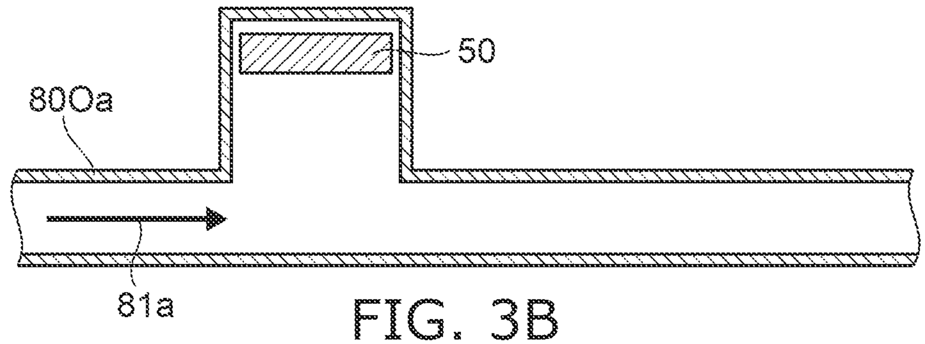
Figure 3C:
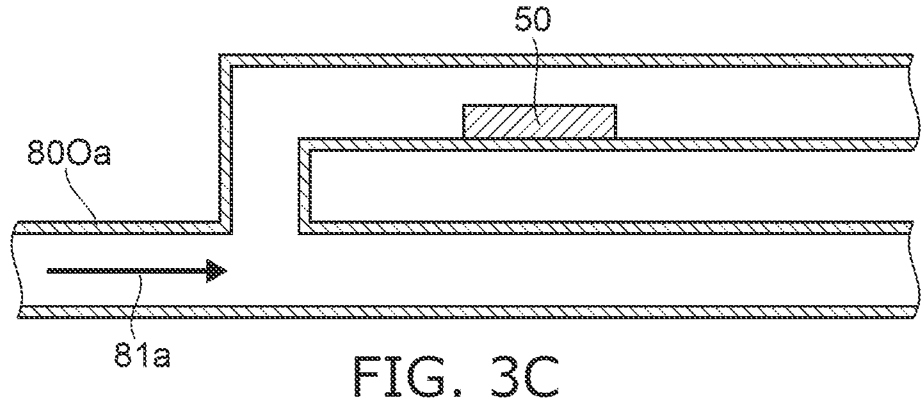
Figure 3D:
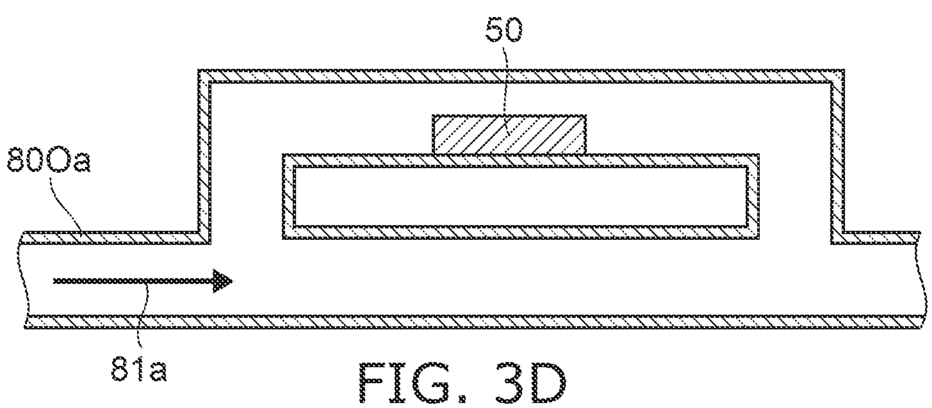

As shown in FIG. 3A, the sensor device 50 may be provided in the first output part 80Oa (e.g. pipe). As shown in FIG. 3B, the sensor device 50 may be provided in a recess provided in the first output part 80Oa (for example, pipe). As shown in FIGS. 3C and 3D, the sensor device 50 may be provided in a branched portion provided in the first output part 80Oa (for example, pipe). As shown in FIG. 3D, the branched portion provided in the first output part 80Oa (for example, pipe) may be detoured and returned to the original portion.

An example of the first concentration sensor 51*c* will be described below. The following description may be applied to the second concentration sensor 52*c*. The first concentration sensor 51*c* may include any of the sensors 110, 110A-110C, 111, 120-122 described below.

Figure 4:
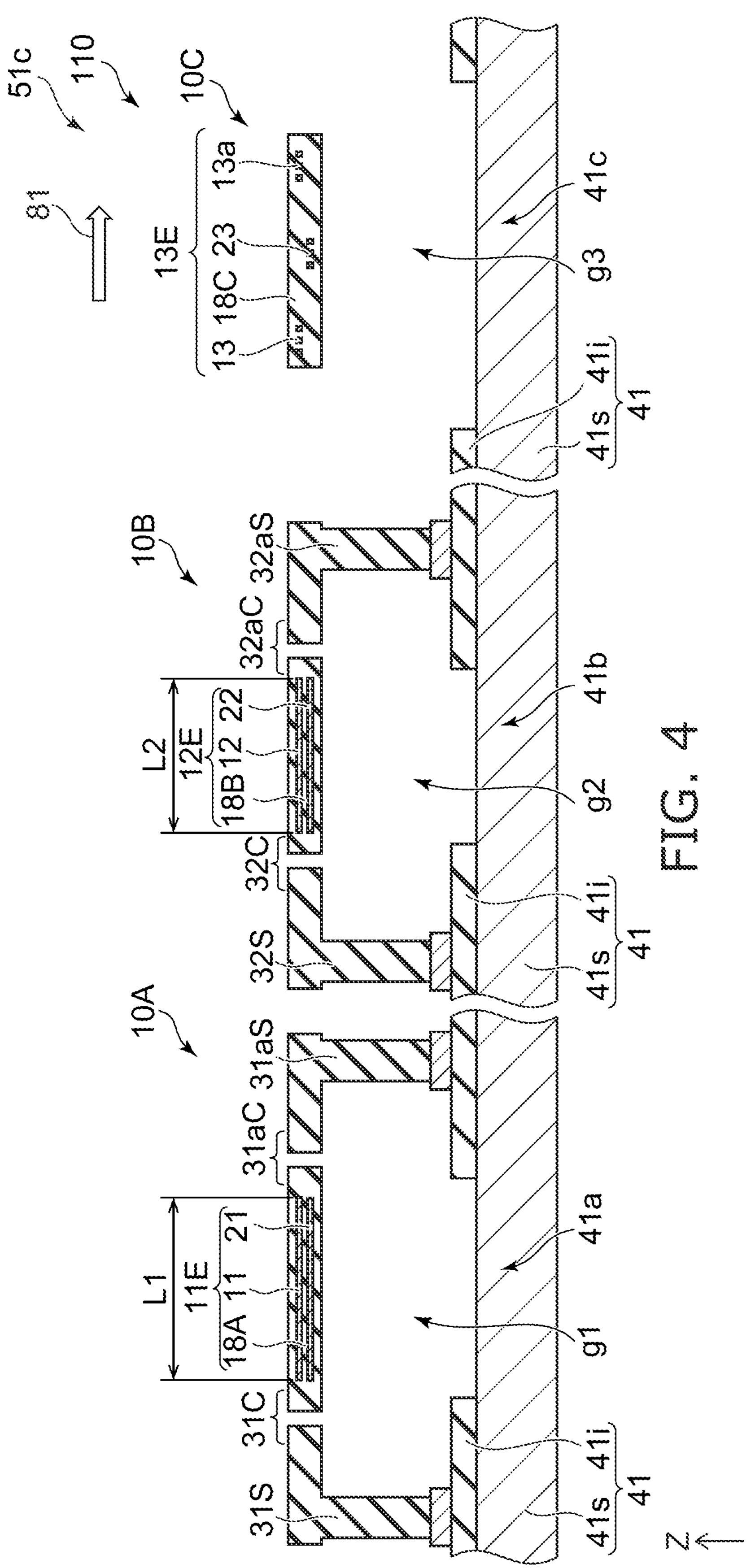
FIG. 4 is a schematic cross-sectional view illustrating a sensor according to the embodiment.

FIG. 4 is a schematic cross-sectional view illustrating a sensor according to the embodiment.

As shown in FIG. 4, a sensor 110 according to the embodiment includes the base 41, the first detection part 10A, the second detection part 10B, and a third detection part 10C.

As shown in FIG. 4, the base 41 includes a first base region 41*a*, a second base region 41*b* and a third base region 41*c*. In this example, the base 41 includes a substrate 41*s* and an insulating film 41*i*. The substrate 41*s* may be, for example, a semiconductor substrate (for example, a silicon substrate). In one example, the base 41 may include a semiconductor. The substrate 41*s* may include, for example, a semiconductor circuit. The substrate 41*s* may include connection members such as via electrodes.

For example, a direction from the first base region 41*a* to the second base region 41*b* is along the upper surface of the base 41, for example. A direction from the first base region 41*a* to the third base region 41*c* is along the upper surface of the base 41, for example. In this example, the first base region 41*a*, the second base region 41*b* and the third base region 41*c* are continuous with each other. As will be described below, these base regions may be spaced apart from each other.

The first detection part 10A includes a first support part 31S, a first connection part 31C, and a first detection element 11E. The first support part 31S is fixed to the base 41. The first support part 31S may be fixed to the base 41 via another member. The first connection part 31C is supported by the first support part 31S. The first connection part 31C supports the first detection element 11E. A first gap g1 is provided between the first base region 41*a* and the first detection element 11E. The first gap g1 is further provided between the first connection part 31C and the first base region 41*a*.

For example, the first detection element 11E includes a first resistance member 11, a first conductive member 21 and a first insulating member 18A. At least a part of the first insulating member 18A is between the first resistance member 11 and the first conductive member 21.

As shown in FIG. 4, the second detection part 10B includes a second support part 32S, a second connection part 32C and a second detection element 12E. The second support part 32S is fixed to the base 41. The second support part 32S may be fixed to the base 41 via another member. The second connection part 32C is supported by the second support part 32S. The second connection part 32C supports the second detection element 12E. A second gap g2 is provided between the second base region 41*b* and the second detection element 12E. The second gap g2 is further provided between the second connection part 32C and the second base region 41*b*.

The second detection element 12E includes a second resistance member 12, a second conductive member 22 and a second insulating member 18B. At least a part of the second insulating member 18B is between the second resistance member 12 and the second conductive member 22.

As shown in FIG. 4, the third detection part 10C includes a third detection element 13E. The third detection element 13E includes a third resistance member 13, a third other resistance member 13*a* and a third conductive member 23. The third conductive member 23 is between the third resistance member 13 and the third other resistance member 13*a*. A third gap g3 is provided between the third base region 41*c* and the third detection element 13E.

As shown in FIG. 4, the third detection element 13E may further include a third insulating member 18C. At least a part of the third insulating member 18C is between the third resistance member 13 and the third conductive member 23 and between the third other resistance member 13*a* and the third conductive member 23.

As will be described later, the third detection element 13E is supported by a third support part 33S and a third connection part 33C (see FIGS. 12A and 12B).

For example, a first current is supplied to the first conductive member 21 from a controller, which will be described later. This increases the temperature of the first detection element 11E. A detection target gas 81 is introduced into the space around the first detection element 11E. The temperature of the first detection element 11E changes (for example, decreases) due to heat conduction by the detection target gas 81. A change in the temperature mainly depends on the type and concentration of the detection target substance included in the detection target gas 81. The change in the temperature also depends on the flow rate of the detection target gas 81. The change in the temperature is detected as a change in an electrical resistance of the first resistance member 11. The first detection part 10A functions at least as the first concentration sensor.

For example, a second current is supplied to the second conductive member 22 from a controller, which will be described later. This increases the temperature of the second detection element 12E. The detection target gas 81 is introduced into the space around the second detection element 12E. The temperature of the second detection element 12E changes (for example, decreases) due to heat conduction by the detection target gas 81. A change in the temperature mainly depends on the type and concentration of the detection target substance included in the detection target gas 81. The change in the temperature also depends on the flow rate of the detection target gas 81. The change in the temperature is detected as a change in an electrical resistance of the first resistance member 11. The second detection part 10B functions at least as the second concentration sensor.

As will be described later, the first detection element 11E and the second detection element 12E have different thermal characteristics. Thermal characteristics include, for example, heat dissipation. Thermal characteristics include, for example, thermal resistance. As a result, different characteristics are obtained with respect to the detection target gas 81 in the multiple detection elements. For example, it becomes possible to detect the concentrations of multiple types of detection target substances included in the detection target gas 81.

On the other hand, a third current is supplied to the third conductive member 23 from a controller, which will be described later. As a result, the temperature of the third resistance member 13 and the third other resistance member 13*a* included in the third detection element 13E rises. For example, the detection target gas 81 flows from the third resistance member 13 to the third other resistance member 13*a*. Due to the flow of the detection target gas 81, a difference occurs between the temperature of the third resistance member 13 and the temperature of the third other resistance member 13*a*. By detecting the electrical resistance of these resistance members, the temperature difference in these resistance members can be detected. The temperature difference mainly depends on the flow rate of the detection target gas 81. The temperature difference also depends on the type and concentration of the detection target substance in the detection target gas 81.

As described above, the detection characteristics of the first detection part 10A (first concentration sensor) depend on the flow rate as well as the concentration. Detection by the second detection part 10B (second concentration sensor) depends on the flow rate in addition to the concentration. Detection by the third detection part 10C (flow rate sensor) depends on the type and concentration of the detection target substance in addition to the flow rate. These detection parts are combined. As a result, the type of the detection target substance and the concentration of the detection target substance may be accurately detected. The flow rate may be accurately detected.

According to the embodiment, it is possible to provide a sensor whose characteristics can be improved. For example, the concentration of each of multiple substances of different types can be detected with high accuracy.

The number of concentration sensors may be any integer of 2 or more. At least one flow rate sensor may be provided. For example, "first detection part" to "nth detection part" are provided. "n" is any integer of 3 or greater. The "nth detection part" is the flow rate sensor (the third detection part 10C in the above example). The "first detection part" to the "(n−1)th detection part" are assumed to be multiple sensors. In this case, the detection values $V_{out1}$ to $V_{outn}$ of the "first detection part" to "nth detection part" are expressed by the following first formula.

$$\left.\begin{aligned} V_{out1} &= f_1(C_1, C_2, C_3, \ldots, C_n, \text{Flow}) \\ V_{out2} &= f_2(C_1, C_2, C_3, \ldots, C_n, \text{Flow}) \\ V_{out3} &= f_3(C_1, C_2, C_3, \ldots, C_n, \text{Flow}) \\ &\vdots \\ V_{out(n-1)} &= f_{n-1}(C_1, C_2, C_3, \ldots, C_n, \text{Flow}) \\ V_{outn} &= f_n(C_1, C_2, C_3, \ldots, C_n, \text{Flow}) \end{aligned}\right\} \quad (1)$$

In the first formula, "$f_1$" to "$f_n$" are functions. "$C_1$" to "$C_n$" are concentrations. "Flow" is the flow rate. By solving the simultaneous equations of the first formula, the concentration and flow rate are obtained as the second formula.

$$C=(C_1, C_2, C_3, \ldots, C_n, \text{Flow}) \quad (2)$$

Calculation of the first formula is performed by a controller, which will be described later. As a result, the concentration of the target substance in the detection target gas 81 is obtained. A further flow rate may be obtained.

As described above, the thermal characteristics are different between the first detection part 10A and the second detection part 10B. Differences in the thermal characteristics are obtained, for example, by several configurations (and combinations thereof) as follows.

For example, an area of the second detection element 12E is different from an area of the first detection element 11E. For example, a length of the second connection part 32C is different from a length of the first connection part 31C. For example, a width of the second connection part 32C is different from a width of the first connection part 31C. For example, a thickness of the second connection part 32C is different from a thickness of the first connection part 31C.

For example, a material of the second connection part 32C is different from a material of the first connection part 31C. For example, a distance between the second base region 41*b* and the second detection element 12E is different than a distance between the first base region 41*a* and the first detection element 11E. Due to at least one of these differences, detection characteristics different from each other are obtained in the multiple detection parts. Examples of such configuration differences will be described later.

As shown in FIG. 4, for example, the first detection part 10A may further include a first other support part 31*a*S and a first other connection part 31*a*C. The first other support portion 31*a*S is fixed to the base 41. The first other connection part 31*a*C is supported by the first other support part 31*a*S. The first other connection part 31*a*C supports the first detection element 11E. The first gap g1 is provided between the first base region 41*a* and the first other connection part 31*a*C. In this example, the first detection element 11E is provided between the first connection part 31C and the first other connection part 31*a*C. The first detection part 10A may have a double-supported beam structure. The configuration of the first other support part 31*a*S may be the same as the configuration of the first support part 31S. The configuration of the first other connection part 31*a*C may be the same as the configuration of the first connection part 31C.

As shown in FIG. 4, for example, the second detection part 10B may further include a second other support part 32*a*S and a second other connection part 32*a*C. The second other support part 32*a*S is fixed to the base 41. The second other connection part 32*a*C is supported by the second other support part 32*a*S. The second other connection part 32*a*C supports the second detection element 12E. The second gap g2 is provided between the second base region 41*b* and the second other connection part 32*a*C. In this example, the second detection element 12E is provided between the second connection part 32C and the second other connection part 32*a*C. The second detection part 10B may have a double-supported beam structure. The configuration of the second other support part 32*a*S may be the same as the configuration of the second support part 32S. The configuration of the second other connection part 32*a*C may be the same as the configuration of the second connection part 32C.

An example of the configuration of the third detection part 10C will be described later.

As shown in FIG. 4, a first direction from the first base region 41*a* to the first detection element 11E is defined as a Z-axis direction. A direction from the second base region 41*b* to the second detection element 12E is along the first direction (Z-axis direction). A direction from the third base region 41*c* to the third detection element 13E is along the first direction (Z-axis direction).

Figure 5:
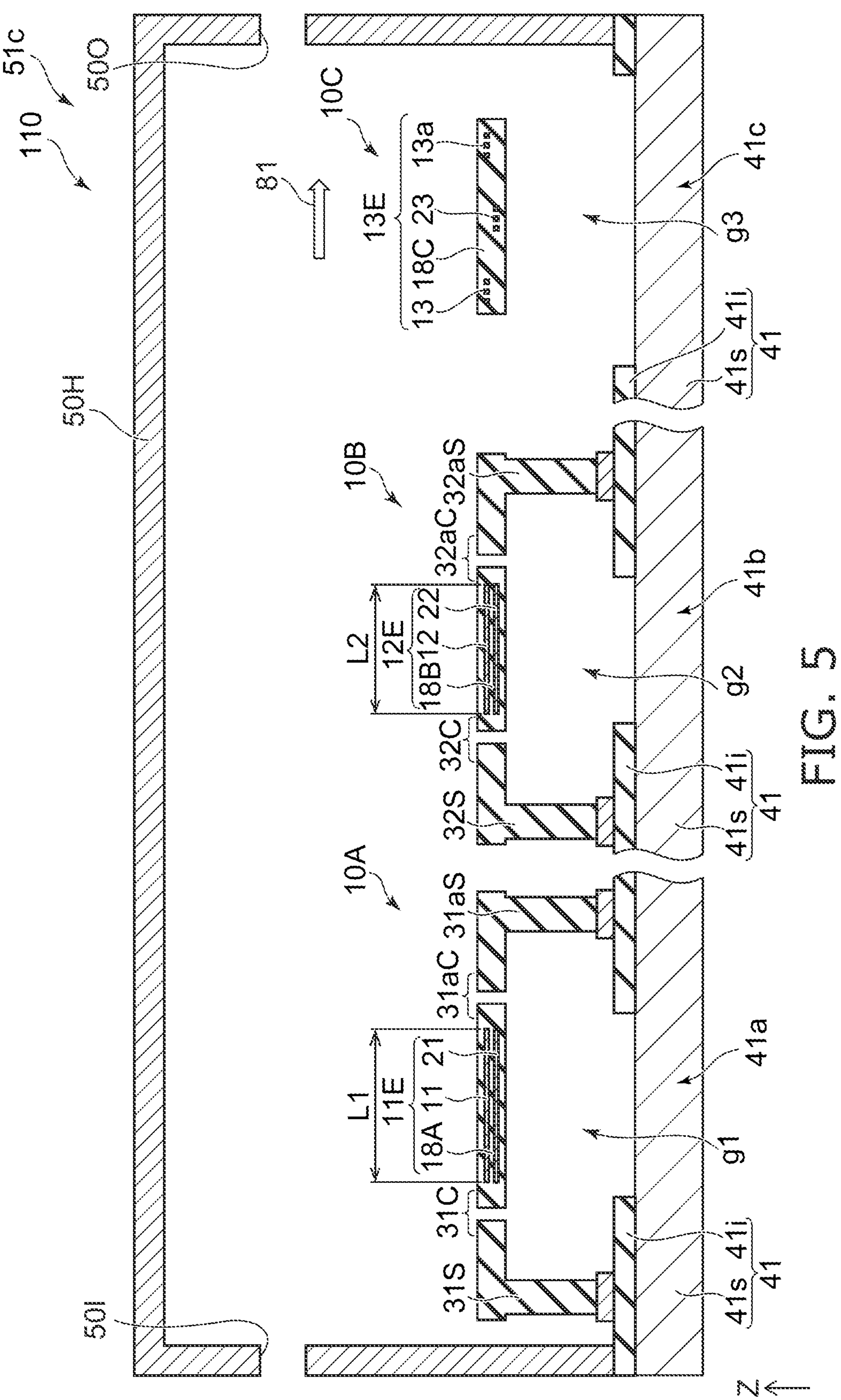
FIG. 5 is a schematic cross-sectional view illustrating the sensor according to the embodiment.

FIG. 5 is a schematic cross-sectional view illustrating the sensor according to the embodiment.

As shown in FIG. 5, the sensor 110 may include a housing 50H. The housing 50H includes an inflow port 50I and an outflow port 50O. The first detection element 11E, the second detection element 12E, and the third detection element 13E are provided between the base 41 and at least a part of the housing 50H. As shown in FIG. 5, a direction from the third resistance member 13 to the third other resistance member 13*a* is along a flow direction of the detection target gas 81 flowing from the inflow port 50I to the outflow port 50O.

Figure 6:
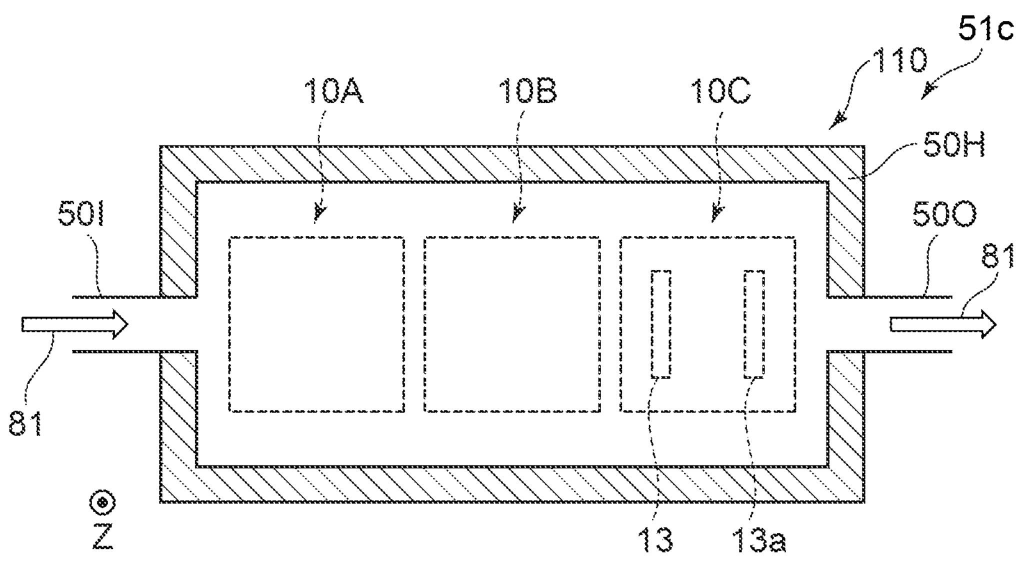
FIG. 6 is a schematic plan view illustrating the sensor according to the embodiment.

FIG. 6 is a schematic plan view illustrating the sensor according to the embodiment.

FIG. 6 is a plan view on an X-Y plane perpendicular to the first direction (Z-axis direction). In FIG. 6, a part of the housing 50H is omitted. As shown in FIG. 6, also in this example, a direction from the third resistance member 13 to the third other resistance member 13*a* is along the flow direction of the detection target gas 81 flowing from the inflow port 50I to the outflow port 50O. In this example, a direction from the third resistance member 13 to the third other resistance member 13*a* is along the direction from the first detection part 10A to the second detection part 10B. In this example, the second detection part 10B is between the first detection part 10A and the third detection part 10C on the plane perpendicular to the Z-axis direction. Various modifications are possible for the mutual positional relationship among the first detection part 10A, the second detection part 10B, and the third detection part 10C.

Figure 7:
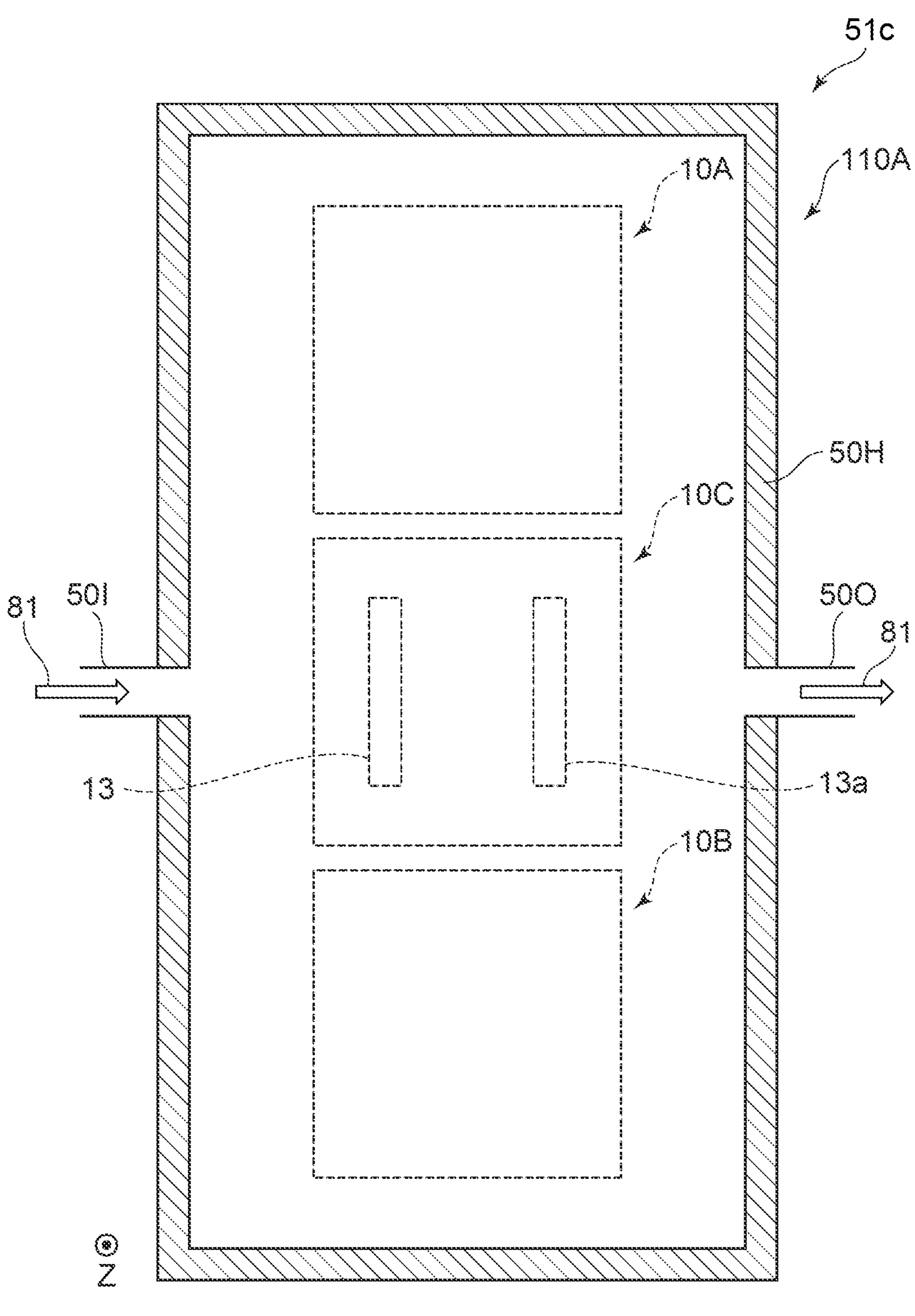
FIG. 7 is a schematic plan view illustrating a sensor according to the embodiment.

FIG. 7 is a schematic plan view illustrating a sensor according to the embodiment.

As shown in FIG. 7, a sensor 110A according to the embodiment is also provided with the first detection part 10A, the second detection part 10B, and the third detection part 10C. In the sensor 110A, a direction from the third resistance member 13 to the third other resistance member 13*a* crosses the direction from the first detection part 10A to the second detection part 10B. Other configurations of the sensor 110A may be the same as those of the sensor 110. In the sensor 110A as well, the direction from the third resistance member 13 to the third other resistance member 13*a* is along the flow direction of the detection target gas 81 flowing from the inflow port 50I to the outflow port 50O.

Figure 8:
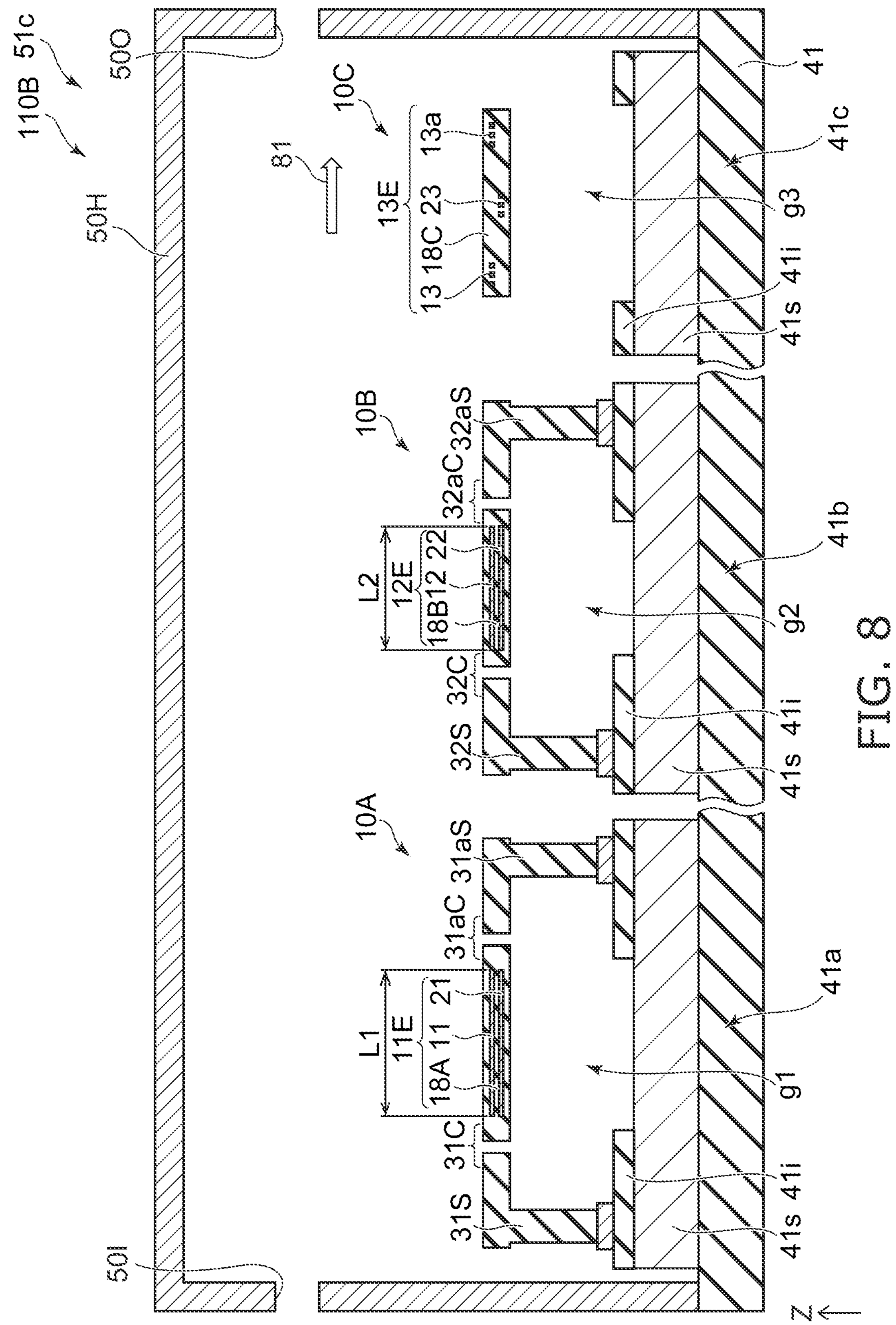
FIG. 8 is a schematic cross-sectional view illustrating a sensor according to the embodiment.

FIG. 8 is a schematic cross-sectional view illustrating a sensor according to the embodiment.

As shown in FIG. 8, a sensor 110B according to the embodiment includes the base 41, the first detection part 10A, the second detection part 10B, the third detection part 10C and the housing 50H. In the sensor 110B, the base 41 is a structure separate from the substrate 41*s*. A substrate 41*s* on which the first detection part 10A is provided is provided in the first base region 41*a*. The substrate 41*s* on which the second detection part 10B is provided is provided in the second base region 41*b*. The substrate 41*s* on which the third detection part 10C is provided is provided in the third base region 41*c*. These substrates 41*s* are separated from each other. Except for this, the configuration of the sensor 110B may be the same as the sensor 110 or the sensor 110A.

In the sensor 110B, the base 41 may be regarded as a part of the housing 50H. The first detection part 10A is provided between the first base region 41*a* of the base 41 and a part of the housing 50H. The second detection part 10B is provided between the second base region 41*b* of the base 41 and a part of the housing 50H. The third detection part 10C is provided between the third base region 41*c* of the base 41 and a part of the housing 50H.

Figure 9:
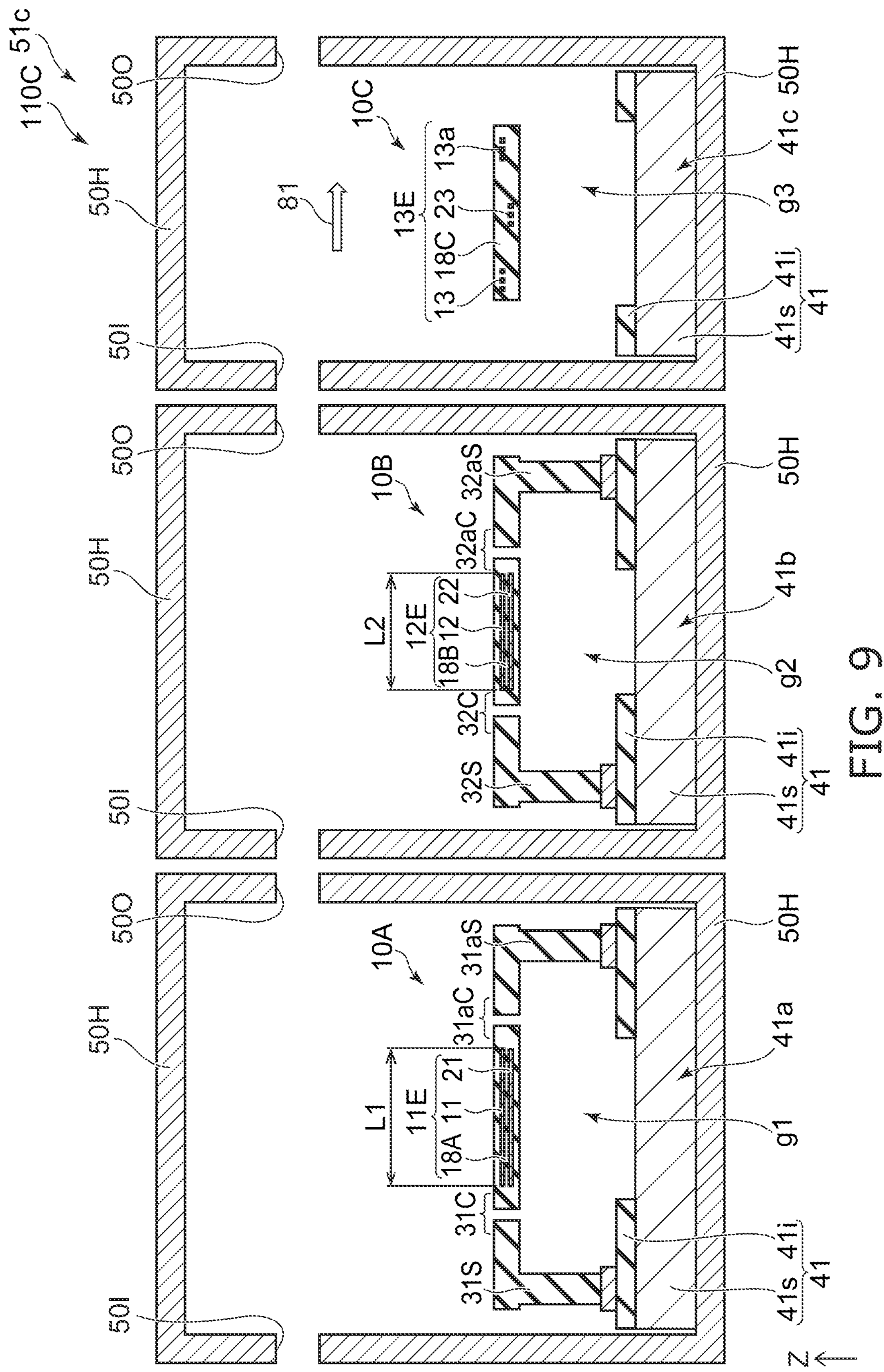
FIG. 9 is a schematic cross-sectional view illustrating a sensor according to the first embodiment.

FIG. 9 is a schematic cross-sectional view illustrating a sensor according to the first embodiment.

As shown in FIG. 9, a sensor 110C according to the embodiment includes the base 41, the first detection part 10A, the second detection part 10B, the third detection part 10C and the housing 50H. In sensor 110C, the first base region 41*a*, the second base region 41*b* and the third base region 41*c* are separated from each other. Except for this, the configuration of the sensor 110C may be the same as the sensor 110 or the sensor 110A.

Thus, in the embodiment, at least two of the first base region 41*a*, the second base region 41*b*, and the third base region 41*c* may be discontinuous.

In this example, the multiple housings 50H are provided. A first detection module including the first detection part 10A may be provided between the first base region 41*a* and a part of one of the multiple housings 50H. A second detection module including the second detection part 10B may be provided between the second base region 41*b* and another part of the multiple housings 50H. A second detection module including the third detection part 10C may be provided between the third base region 41*c* and another part of the multiple housings 50H.

Each of the first base region 41*a*, the second base region 41*b*, and the third base region 41*c* may be a part of the housing 50H.

Examples of configurations of the first detection part 10A, the second detection part 10B, and the third detection part 10C will be further described below.

Figure 10A:
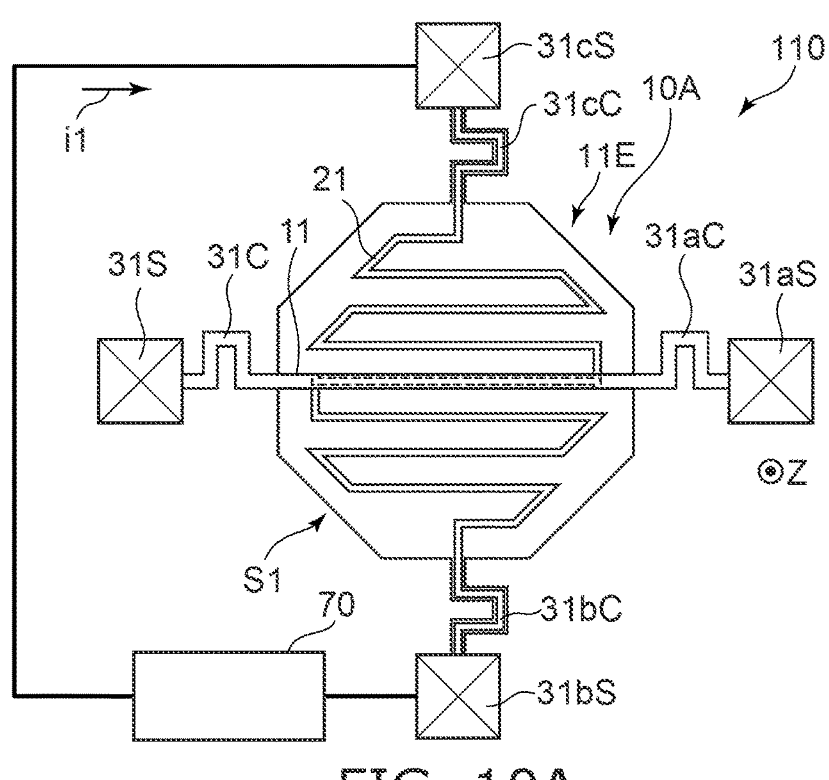
FIGS. 10A and 10B are schematic plan views illustrating a part of the sensor according to the embodiment.
Figure 10B:
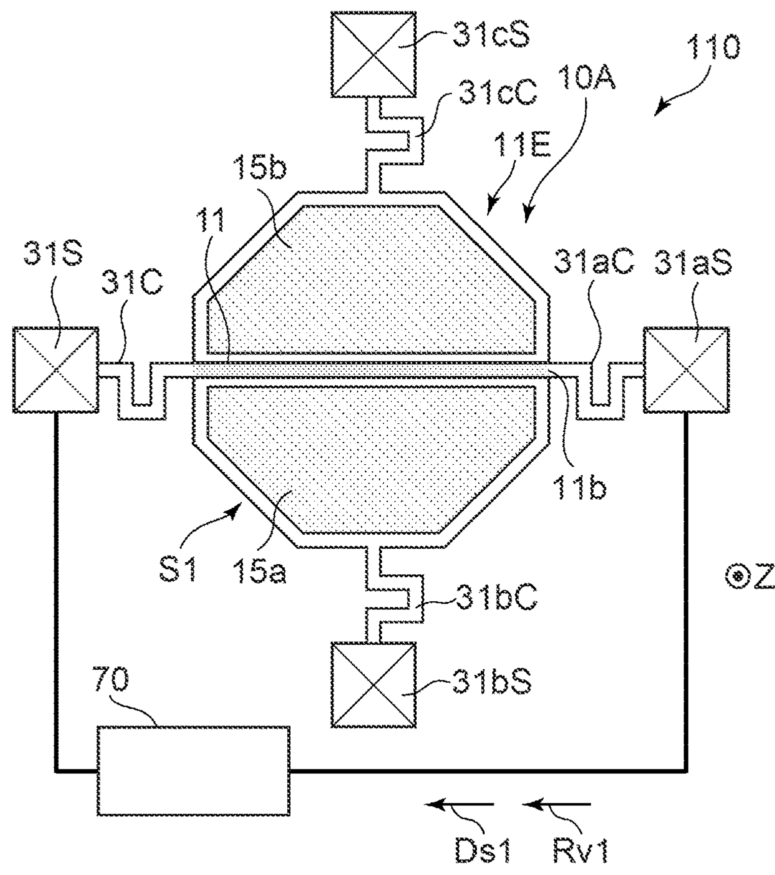

FIGS. 10A and 10B are schematic plan views illustrating a part of the sensor according to the embodiment.

These figures illustrate the first detection part 10A. FIG. 10A illustrates a planar pattern of the first conductive member 21. FIG. 10B illustrates a planar pattern of the first resistance member 11.

As shown in FIGS. 10A and 10B, in this example, the first detection element 11E (the portion including the first resistance member 11, the first conductive member 21 and the first insulating member 18A) is octagonal. The planar shape of the first detection element 11E is arbitrary. The first detection element 11E has a first area 51. The first area 51 is an area of the first detection element 11E on the plane crossing the first direction (Z-axis direction) from the first base region 41*a* to the first detection element 11E.

As shown in FIGS. 10A and 10B, a controller 70 may be provided. The controller 70 can be electrically connected to the first resistance member 11 and the first conductive member 21. For example, the controller 70 supplies the first current i1 to the first conductive member 21 to raise the temperature of the first detection element 11E.

The first detection part 10A may further include a support part 31*b*S and a connection part 31*b*C. The support part 31*b*S is fixed to the base 41. The connection part 31*b*C is supported by the support part 31*b*S. The connection part 31*b*C supports the first detection element 11E.

The first detection part 10A may further include a support part 31*c*S and a connection part 31*c*C. The support part 31*c*S is fixed to the base 41. The connection part 31*c*C is supported by the support part 31*c*S. The connection part 31*c*C supports the first detection element 11E. The first detection element 11E is provided between the connection part 31*b*C and the connection part 31*c*C.

The first current i1 may be supplied to the first conductive member 21 via the support part 31*b*S, the connection part 31*b*C, the support part 31*c*S and the connection part 31*c*C.

As shown in FIG. 10B, the controller 70, for example, may be electrically connected to the first resistance member 11 via the first support part 31S, the first connection part 31C, the first other support part 31*a*S, and the first other connection part 31*a*C.

As shown in FIG. 10B, the first detection element 11E may include a first layer 15*a* and a second layer 15*b*. The first layer 15*a* and the second layer 15*b* may include the same material and thickness as the first resistance member 11. The first resistance member 11 is provided between the first layer 15*a* and the second layer 15*b*. By providing these layers, deformation (for example, warpage) of the first detection element 11E is suppressed.

Figure 11A:
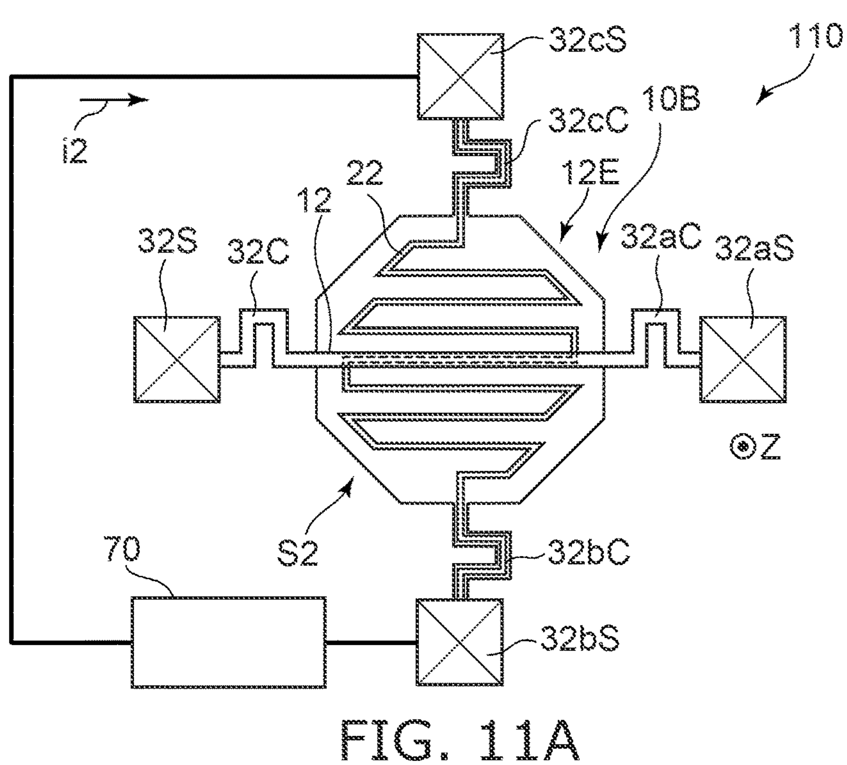
FIGS. 11A and 11B are schematic plan views illustrating a part of the sensor according to the embodiment.
Figure 11B:
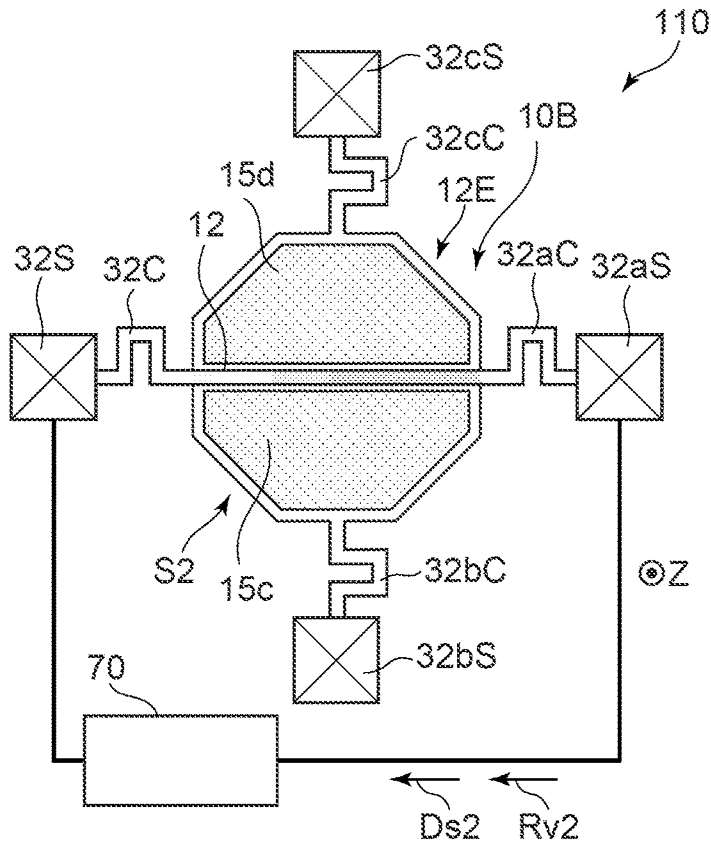

FIGS. 11A and 11B are schematic plan views illustrating a part of the sensor according to the embodiment.

These figures illustrate the second detection part 10B. FIG. 11A illustrates a plane pattern of the second conductive member 22. FIG. 11B illustrates a plane pattern of the second resistance member 12.

As shown in FIGS. 11A and 11B, in this example, the second detection element 12E (the portion including the second resistance member 12, the second conductive member 22 and the second insulating member 18B) is octagonal. The planar shape of the second detection element 12E is arbitrary. The second detection element 12E has a second area S2. The second area S2 is an area of the second detection element 12E on a plane crossing the first direction (Z-axis direction). In this example, the second area S2 is different from the first area 51. In this example, the second area S2 is smaller than the first area 51.

As shown in FIGS. 11A and 11B, the controller 70 can be electrically connected to the second resistance member 12 and the second conductive member 22. For example, the controller 70 supplies the second current i2 to the second conductive member 22 to raise the temperature of the second detection element 12E.

The second detection part 10B may further include a support part 32*b*S and a connection part 32*b*C. The support part 32*b*S is fixed to the base 41. The connection part 32*b*C is supported by the support part 32*b*S. The connection part 32*b*C supports the second detection element 12E.

The second detection part 10B may further include a support part 32*c*S and a connection part 32*c*C. The support part 32*c*S is fixed to the base 41. The connection part 32*c*C is supported by the support part 32*c*S. The connection part 32*c*C supports the second detection element 12E. The second detection element 12E is provided between the connection part 32*b*C and the connection part 32*c*C.

The second current i2 may be supplied to the second conductive member 22 via the support part 32*b*S, the connection part 32*b*C, the support part 32*c*S and the connection part 32*c*C.

As shown in FIG. 11B, the controller 70, for example, may be electrically connected to the second resistance member 12 via the second support part 32S, the second connection part 32C, the second other support part 32*a*S, and the second other connection part 32*a*C.

As shown in FIG. 11B, the second detection element 12E may include a third layer 15*c* and a fourth layer 15*d*. The third layer 15*c* and the fourth layer 15*d* may include the same material and thickness as the second resistance member 12. The second resistance member 12 is provided between the third layer 15*c* and the fourth layer 15*d*. Deformation (for example, warpage) of the second detection element 12E is suppressed by providing these layers.

As shown in FIG. 4, the first detection element 11E has a first length L1 in a direction (e.g. second direction) crossing the first direction (Z-axis direction). The second detection element 12E has a second length L2 in a direction (e.g. second direction) crossing the first direction (Z-axis direction). In this example, the second length L2 is shorter than the first length L1. A difference in area is obtained.

Figure 12A:
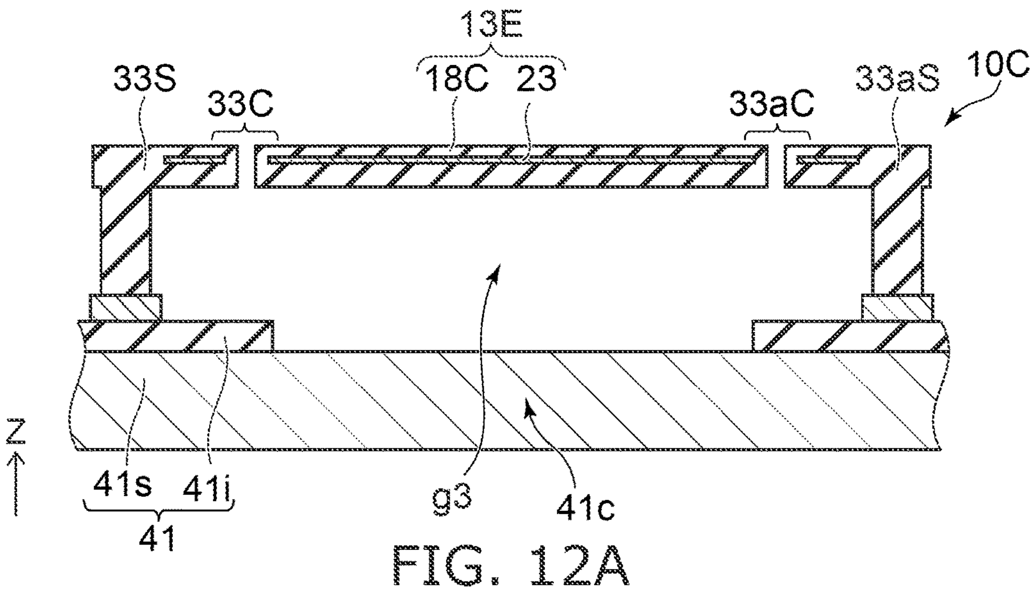
FIGS. 12A and 12B are schematic views illustrating a part of the sensor according to the embodiment.
Figure 12B:
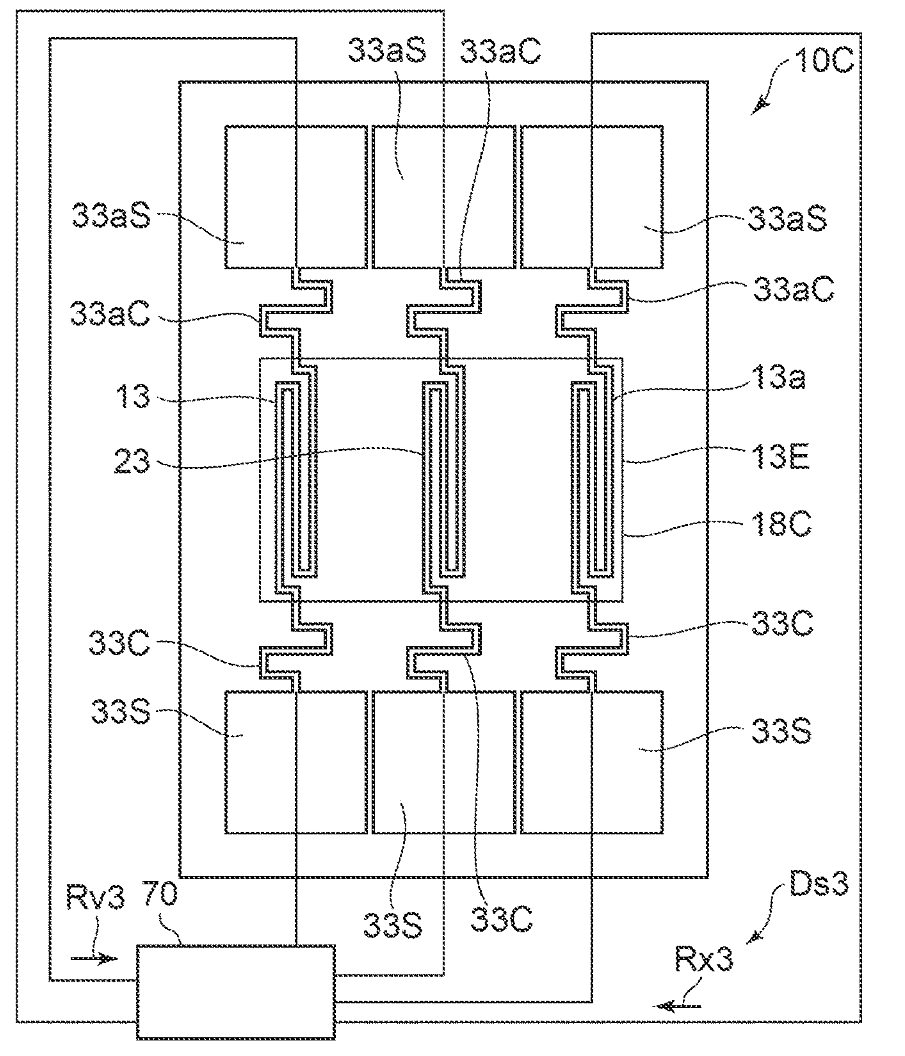

FIGS. 12A and 12B are schematic views illustrating a part of the sensor according to the embodiment.

These figures illustrate the third detection part 10C. FIG. 12A is a cross-sectional view. FIG. 12B is a plan view.

As shown in FIG. 12A, for example, the third detection part 10C may include a third support part 33S and a third connection part 33C. The third support part 33S is fixed to the base 41. The third connection part 33C is supported by the third support part 33S. The third connection part 33C supports the third detection element 13E. The third gap g3 is provided between the third base region 41*c* and the third connection part 33C.

As shown in FIG. 12A, for example, the third detection part 10C may further include a third other support part 33*a*S and a third other connection part 33*a*C. The third other support part 33*a*S is fixed to the base 41. The third other connection part 33*a*C is supported by the third other support part 33*a*S. The third other connection part 33*a*C supports the third detection element 13E. The third gap g3 is provided between the third base region 41*c* and the third other connection part 33*a*C. In this example, the third detection element 13E is provided between the third connection part 33C and the third other connection part 33*a*C. The third detection part 10C may have a double-supported beam structure.

As shown in FIG. 12B, in this example, three sets of third support part 33S and third connection part 33C are provided. Three sets of the third other support part 33*a*S and the third other connection part 33*a*C are provided. The controller 70 is electrically connected to the third resistance member 13 via one third connection part 33C and one third other connection part 33*a*C. The controller 70 is electrically connected to the third other resistance member 13*a* via another one third connection part 33C and another one third other connection part 33*a*C. The controller 70 is electrically connected to the third conductive member 23 via another third connection part 33C and another third other connection part 33*a*C.

The controller 70 supplies a current to the third conductive member 23 to raise the temperature of the third detection element 13E. The controller 70 can detect the difference between the electrical resistance of the third resistance member 13 and the electrical resistance of the third other resistance member 13*a*. The flow rate of the detection target gas 81 is detected based on the detection result of the difference.

The sensor (e.g. sensor 110, etc.) according to the embodiment may include the controller 70 (see FIGS. 10A and 10B, etc.). The controller 70 can obtain first detection data Ds1 (see FIG. 10B) obtained from the first detection part 10A. The controller 70 can obtain second detection data Ds2 (see FIG. 11B) obtained from the second detection part 10B. The controller 70 can obtain third detection data Ds3 (see FIG. 12B) obtained from the third detection part 10C. The controller 70 can derive the concentration of the detection target gas 81 and the flow rate of the detection target gas 81 based on the first detection data Ds1, the second detection data Ds2, and the third detection data Ds3. The concentration of the detection target gas 81 includes the concentrations of each of the multiple types of detection target substances included in the detection target gas 81.

The multiple types of detection target substances may include, for example, at least two selected from the group consisting of carbon dioxide, carbon monoxide, hydrogen, oxygen and water. Multiple types of detection target substances are optional.

The first detection data Ds1 includes a first value Rv1 (see FIG. 10B) corresponding to the electrical resistance of the first resistance member 11. The second detection data Ds2 includes a second value Rv2 corresponding to the electrical resistance of the second resistance member 12 (see FIG. 11B). The third detection data Ds3 includes a third value Rv3 corresponding to the electrical resistance of the third resistance member 13 and a third other value Rx3 corresponding to the electrical resistance of the third other resistance member 13*a* (see FIG. 12B). The first value Rv1, the second value Rv2, the third value Rv3, and the third other value Rx3 change according to the concentration of the detection target gas 81 and the flow rate of the detection target gas 81.

The controller 70 can derive the concentration of the detection target gas 81 and the flow rate of the detection target gas 81 based on these values. In the derivation, the first and second formulae above are used.

An example in which a distance between the second base region 41*b* and the second detection element 12E is different from a distance between the first base region 41*a* and the first detection element 11E will be described below.

Figure 13A:
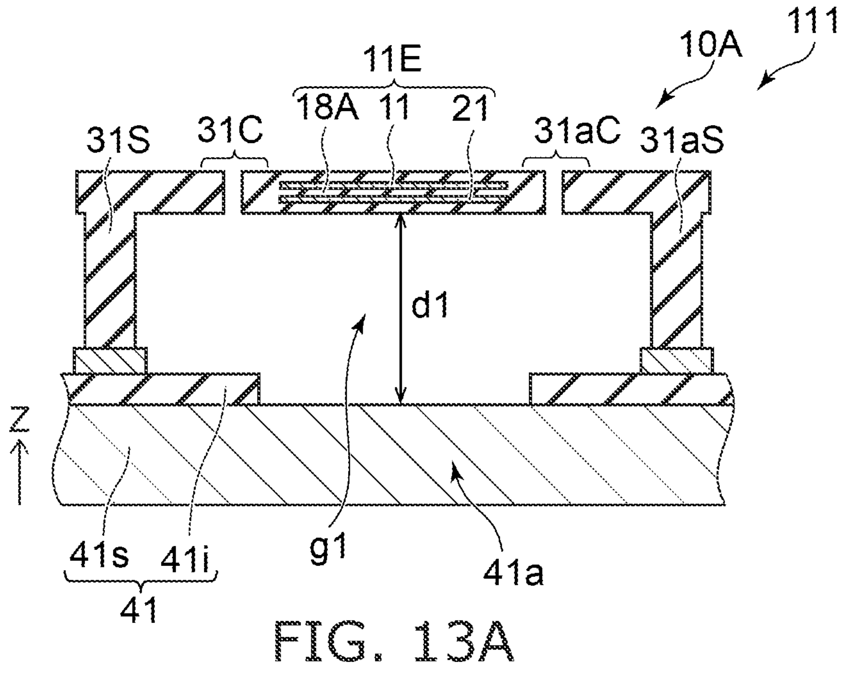
FIGS. 13A and 13B are schematic cross-sectional views illustrating a sensor according to the embodiment.
Figure 13B:
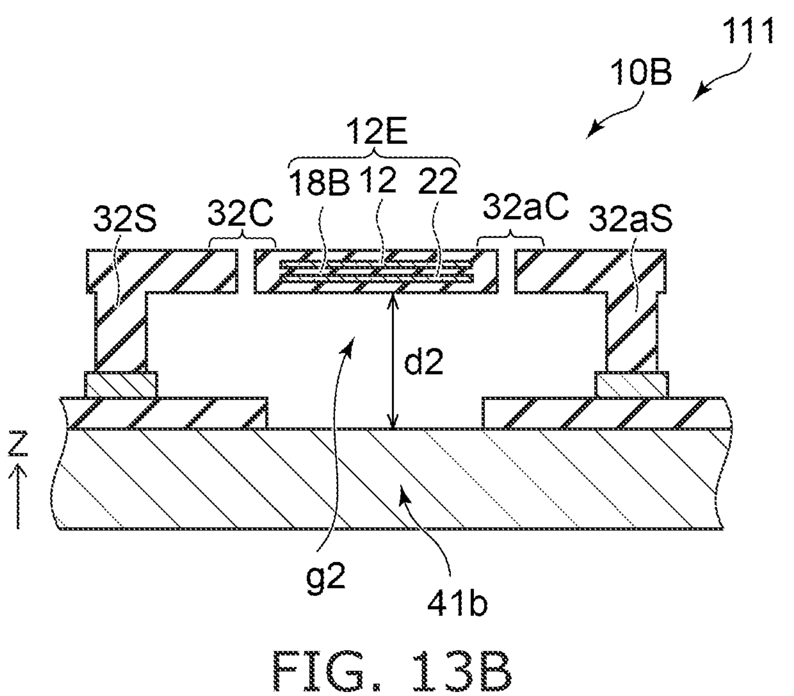

FIGS. 13A and 13B are schematic cross-sectional views illustrating a sensor according to the embodiment.

FIG. 13A illustrates the first detection element 11E. FIG. 13B illustrates the second detection element 12E. As shown in FIGS. 13A and 13B, in a sensor 111 according to the embodiment, a height with respect to the base 41 is different between the first detection element 11E and the second detection element 12E. Except for this, the configuration of the sensor 111 may be the same as that of the sensor 110, for example.

In the sensor 111, a first distance d1 in the first direction (Z-axis direction) between the first base region 41*a* and the first detection element 11E is a distance between the second base region 41*b* and the second detection element 12E. It is different from a second distance d2 in the first direction. Since these distances are different from each other, the heat dissipation characteristics from these detection elements via the base 41 are different. The different heat dissipation characteristics are obtained. Using the difference in the heat dissipation characteristics enables detection with higher accuracy.

Some examples of differences in the configuration of the connection parts are described below.

Figure 14A:
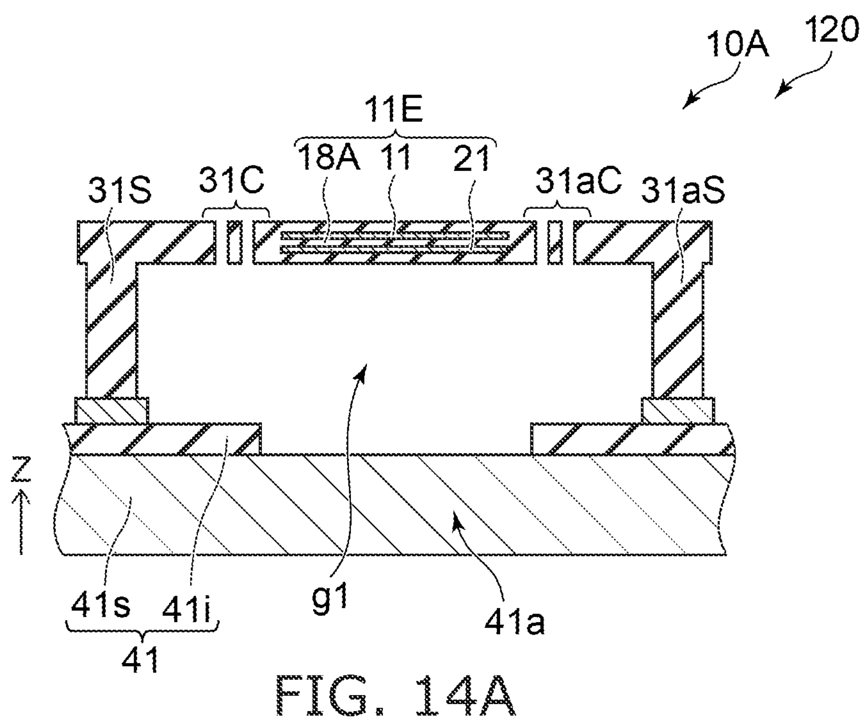
FIGS. 14A and 14B are schematic cross-sectional views illustrating a sensor according to the embodiment.
Figure 14B:
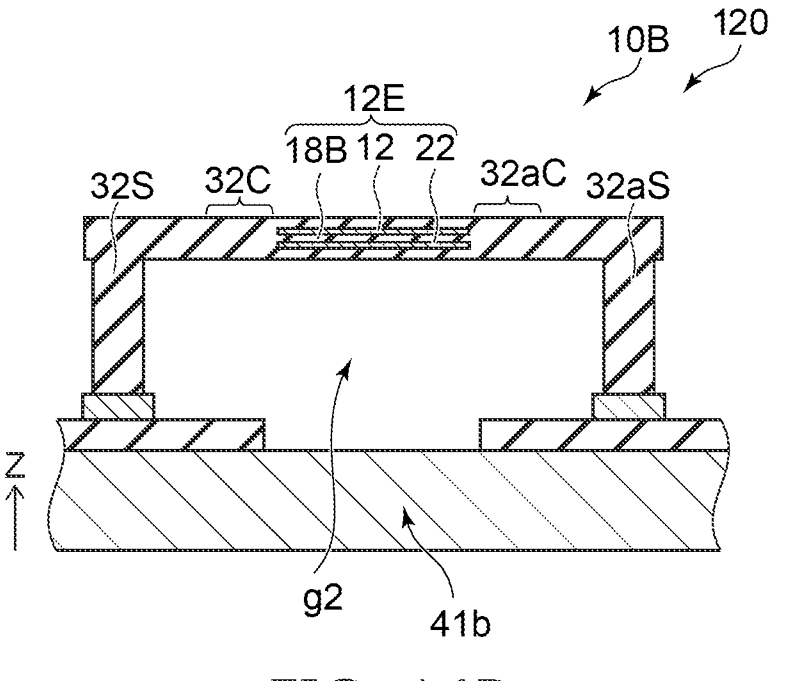

FIGS. 14A and 14B are schematic cross-sectional views illustrating a sensor according to the embodiment.

Figure 15A:
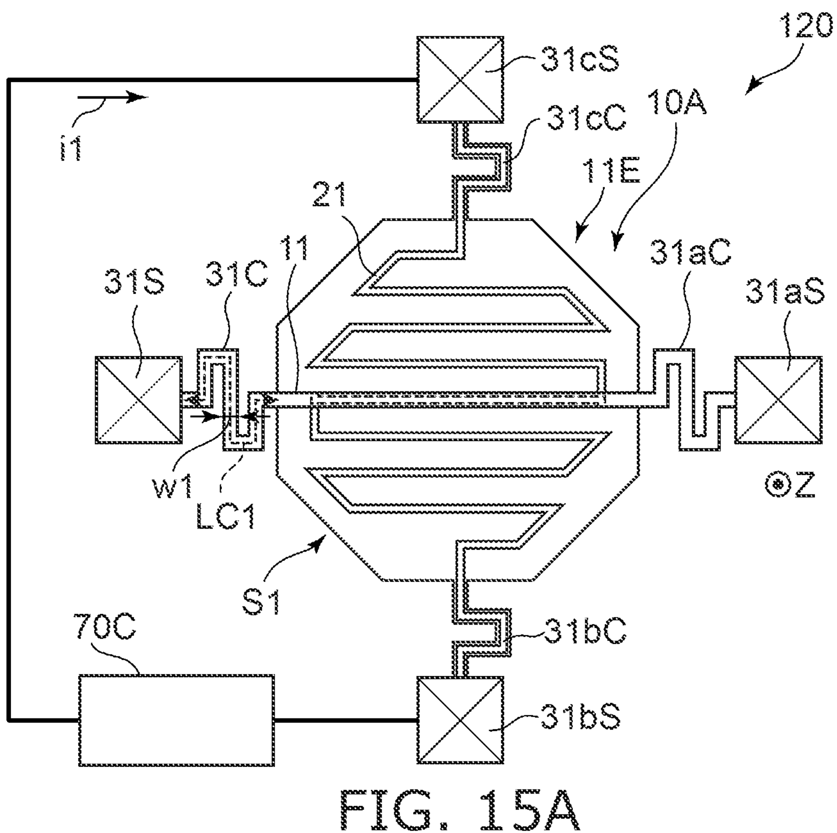
FIGS. 15A and 15B are schematic plan views illustrating the sensor according to the embodiment.
Figure 15B:
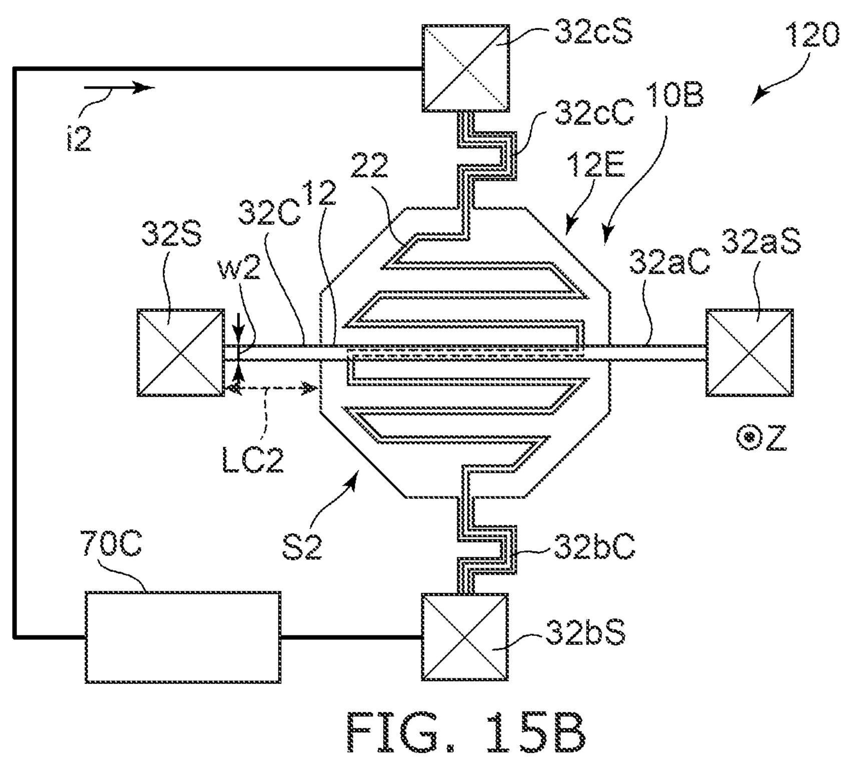

FIGS. 15A and 15B are schematic plan views illustrating the sensor according to the embodiment.

FIGS. 14A and 15A illustrate the first detection element 11E. FIGS. 14B and 15B illustrate the second detection element 12E.

As shown in FIGS. 14A, 14B, 15A and 15B, in a sensor 120 according to the embodiment, a length of the first connection part 31C and a length of the second connection part 32C are differ from each other. Except for this, the configuration of the sensor 120 may be the same as that of the sensor 110, for example.

As shown in FIG. 15A, in this example, the first connection part 31C has a meandering spring structure. On the other hand, as shown in FIG. 15B, the second connection part 32C is linear.

As shown in FIG. 15A, the first connection part 31C has a first connection part length LC1. The first connection part length LC1 is a length of the first connection part 31C along a path (first connection part path) between the first support part 31S and the first detection element 11E.

As shown in FIG. 15B, the second connection part 32C has a second connection part length LC2. The second connection part length LC2 is a length of the second connection part 32C along a path (second connection part path) between the second support part 32S and the second detection element 12E. The second connection part length LC2 is different from the first connection part length LC1.

As shown in FIG. 15A, the first connection part 31C has a first connection part width w1. The first connection part width w1 is a width of the first connection part 31C along the first connection part path between the first support part 31S and the first detection element 11E.

As shown in FIG. 15B, the second connection part 32C has a second connection part width w2. The second connection part width w2 is a width of the second connection part 32C in a direction crossing the second connection part path between the second support part 32S and the second detection element 12E. The second connection part width w2 may be different from the first connection part width w1. The difference in widths provides a difference in the thermal resistance of the connection part. A difference in the heat dissipation characteristics through the connection part can be used.

Figure 16A:
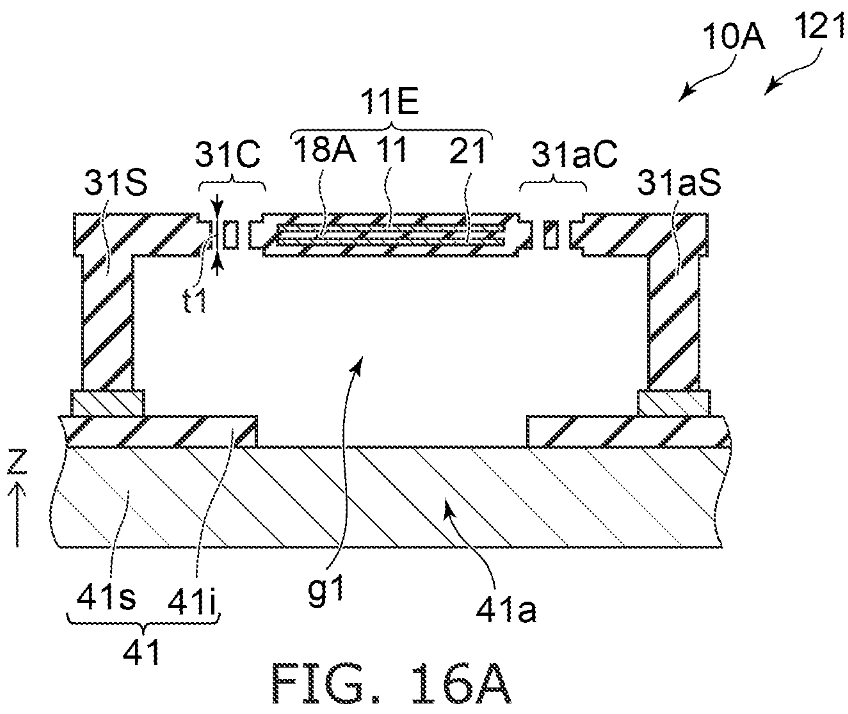
FIGS. 16A and 16B are schematic cross-sectional views illustrating a sensor according to the embodiment.
Figure 16B:
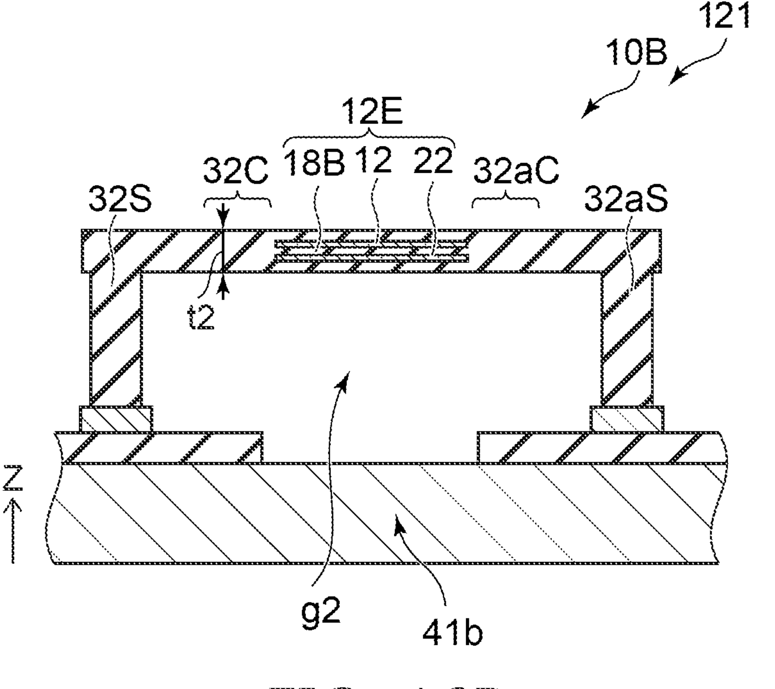

FIGS. 16A and 16B are schematic cross-sectional views illustrating a sensor according to the embodiment.

FIG. 16A illustrates the first detection element 11E. FIG. 16B illustrates the second detection element 12E. As shown in FIGS. 16A and 16B, in a sensor 121 according to the embodiment, a thickness of the first connection part 31C and a thickness of the second connection part 32C are different from each other. Except for this, the configuration of the sensor 121 may be the same as that of the sensor 110, for example.

As shown in FIG. 16A, in the sensor 121 according to the embodiment, the first connection part 31C has a first connection part thickness t1. The first connection part thickness t1 is a thickness of the first connection part 31C in the first direction (Z-axis direction).

As shown in FIG. 16B, the second connection part 32C has a second connection part thickness t2. The second connection part thickness t2 is a thickness of the second connection part 32C in the first direction (Z-axis direction). The second connection part thickness t2 is different from the first connection part thickness t1. This thickness difference provides a difference in the thermal resistance of the connection part. For example, a difference in the heat dissipation characteristics through the connection part can be used.

Figure 17A:
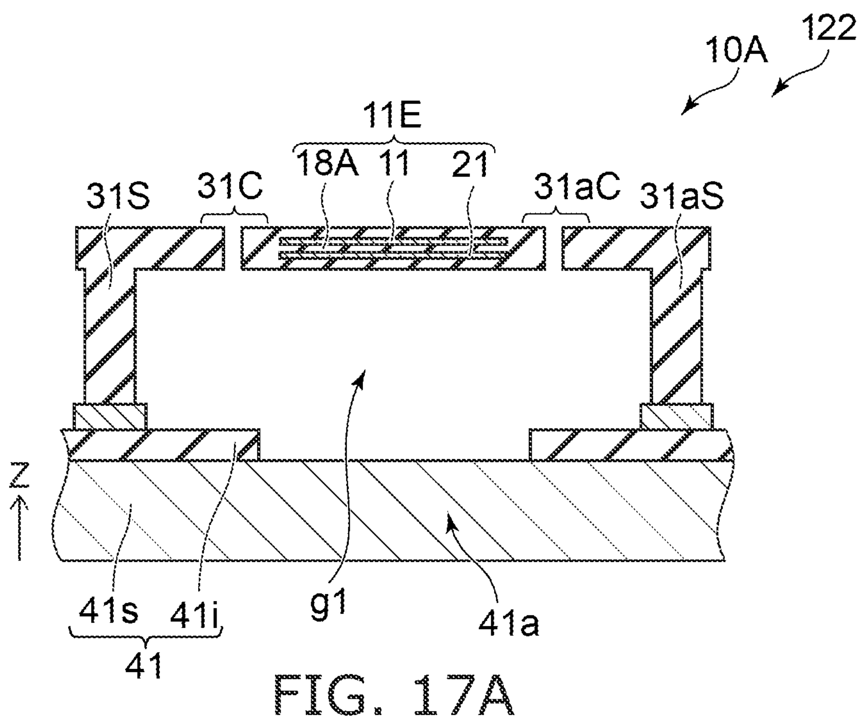
FIGS. 17A and 17B are schematic cross-sectional views illustrating a sensor according to the embodiment.
Figure 17B:
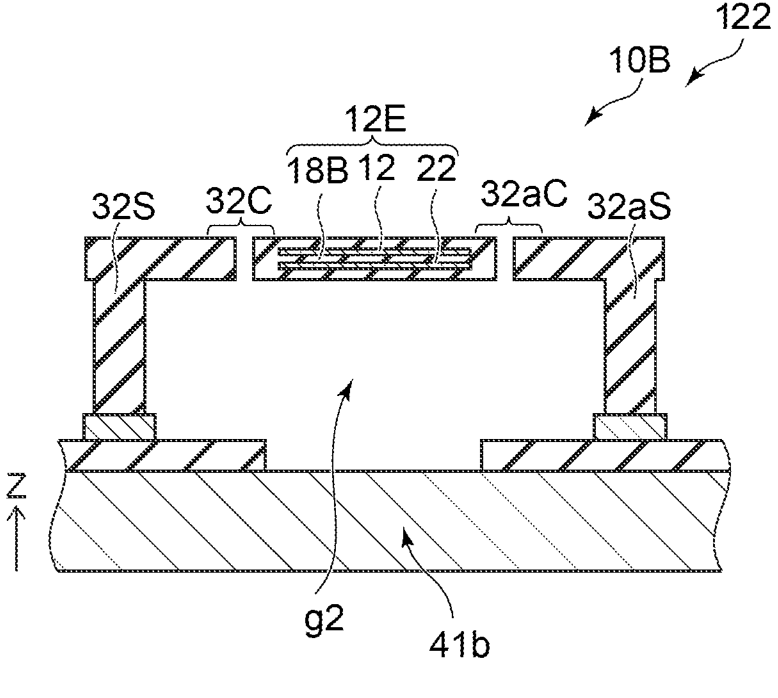

FIGS. 17A and 17B are schematic cross-sectional views illustrating a sensor according to the embodiment.

FIG. 17A illustrates the first detection element 11E. FIG. 17B illustrates the second detection element 12E. In a sensor 122 according to the embodiment shown in FIGS. 17A and 17B, a thickness and a material of the first connection part 31C and a material of the second connection part 32C are different from each other. Except for this, the configuration of the sensor 122 may be the same as that of the sensor 110, for example.

In the sensor 122, the first connection part 31C includes a first connection part material. The second connection part 32C includes a second connection part material different from the first connection part material. This material difference provides a difference in the thermal resistance of the connection part. For example, a difference in the heat dissipation characteristics through the connection part can be used.

At least two of the configurations described above with respect to the sensors 111 and 120-122 may be combined.

In the embodiment, as already described, the first detection part 10A has the first area S1 of the first detection element 11E, the first connection part length LC1 of the first connection part 31C, the first connection part width w1 of the first connection part 31C, the first connection part thickness t1 of the first connection part 31C, the first connection part material of the first connection part 31C, and the first distance d1. The first distance d1 is a distance between the first base region 41*a* and the first detection element 11E.

The second detection part 10B has at least one of the second area S2 different from the first area S1 of the second detection element 12E, the second connection part length LC2 different from the first connection part length LC1 of the second connection part 32C, the second connection part width w2 different from the first connection part width w1 of the second connection part 32C, the second connection part thickness t2 different from the first connection part thickness t1 of the second connection part 32C, the second connection part material different from the first connection part material of the second connection part 32C, or the second distance d2 different from the first distance d1. The second distance d2 is a distance between the second base region 41*b* and the second detection element 12E.

With such a configuration, it is possible to detect the concentration of the detection target substance with higher accuracy. According to the embodiment, it is possible to provide a sensor whose characteristics can be improved. For example, the concentration of each of multiple substances of different types can be detected with high accuracy. The flow rate of the detection target gas 81 may be detected.

The first area S1 is an area of the first detection element 11E on the plane crossing the first direction (Z-axis direction) from the first base region 41*a* to the first detection element 11E. The second area S2 is an area of the second detection element 12E on this plane.

The first connection part length LC1 is a length of the first connection part 31C along the first connection part path between the first support part 31S and the first detection element 11E. The first connection part width w1 is a width of the first connection part 31C in a direction crossing the first connection part path. The first connection part thickness t1 is a thickness of the first connection part 31C in the first direction.

The second connection part length LC2 is a length of the second connection part 32C along the second connection part path between the second support part 32S and the second detection element 12E. The second connection part width w2 is a width of the second connection part 32C in a direction crossing the second connection part path. The second connection part thickness t2 is a thickness of the second connection part 32C in the first direction.

The first distance d1 is a distance along the first direction between the first base region 41*a* and the first detection element 11E. The second distance d2 is a distance along the first direction between the second base region 41*b* and the second detection element 12E.

An example of the first flow rate sensor 51*f* will be described below.

Figure 18:
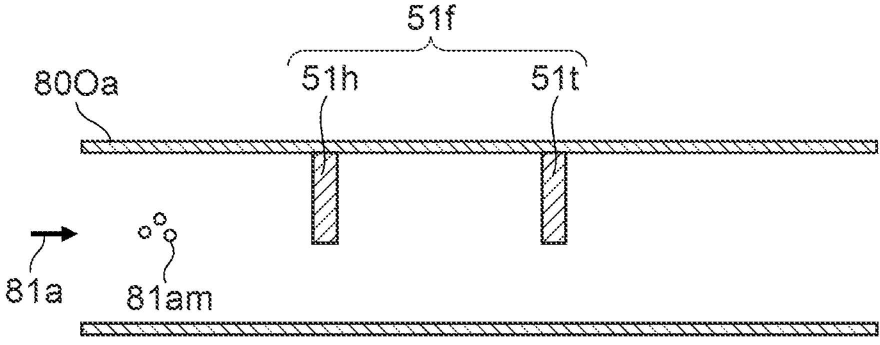
FIG. 18 is a schematic view illustrating a part of the sensor according to the embodiment.

FIG. 18 is a schematic view illustrating a part of the sensor according to the embodiment.

As shown in FIG. 18, the first flow rate sensor 51*f* includes, for example, a heater 51*h* and a temperature sensor 51*t*. For example, the heater 51*h* and the temperature sensor 51*t* are provided in the flow path of the detection target gas (for example, the first output gas 81*a*). The flow path is, for example, the first output part 80Oa. The detection target gas is heated by the heater 51*h*. The temperature of the heated detection target gas is detected by the temperature sensor 51*t*. The temperature detected by the temperature sensor 51*t* depends on the flow rate of the detection target gas. The flow rate can be detected from the result of temperature detection by the temperature sensor 51*t*.

Various modifications are possible for the configuration of the first flow rate sensor 51*f*. The configuration of the second flow rate sensor 52*f* may be the same as the configuration of the first flow rate sensor 51*f*.

Figure 19:
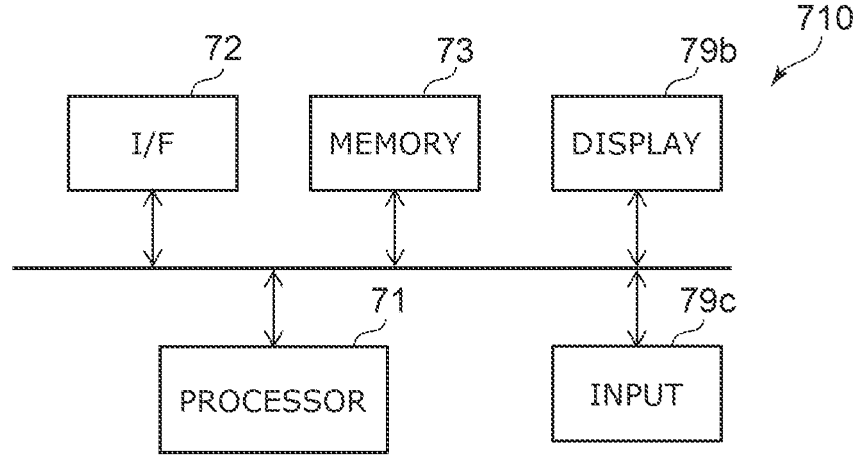
FIG. 19 is a schematic view illustrating a data processing device according to the embodiment.

FIG. 19 is a schematic view illustrating a data processing device according to the embodiment.

As shown in FIG. 19, the data processing device 710 includes the processor 71, the acquisitor 72 and a memory 73. The processor 71 is, for example, an electric circuit. The memory 73 may include, for example, at least one of ROM (Read Only Memory) or RAM (Random Access Memory). Any memory device may be used as the memory 73.

The data processing device 710 may include a display 79*b*, an input 79*c*, and the like. The display 79*b* may include various displays. The input 79*c* includes, for example, a device having an operation function (e.g. keyboard, mouse, touch input panel, voice recognition input device, etc.).

The embodiment may include programs. The program causes a computer (processor 71) to perform the above operations. The embodiment may include a storage medium storing the above program.

Second Embodiment

The second embodiment relates to a gas conversion system (e.g. gas conversion system 310 or gas conversion system 311, etc.).

As already described, the gas conversion system 310 includes the data processing device 710, the first concentration sensor 51*c*, the first flow rate sensor 51*f*, and the gas converter 80 (see FIG. 1). The first output gas 81*a* is output from the gas converter 80. The first concentration sensor 51*c* includes the first detection part 10A including the first detection element 11E, the second detection part 10B including the second detection element 12E, the third detection part 10C including the third detection element 13E, and the base 41 (see FIG. 4). The base 41 includes the first base region 41*a*, the second base region 41*b*, and the third base region 41*c*. The first gap g1 is provided between the first base region 41*a* and the first detection element 11E. The second gap g2 is provided between the second base region 41*b* and the second detection element 12E. The third gap g3 is provided between the third base region 41*c* and the third detection element 13E (see FIG. 4, etc.).

For example, the first detection part 10A further includes the first support part 31S and the first connection part 31C. The first support part 31S is fixed to the base 41. The first connection part 31C is supported by the first support part 31S. The first connection part 31C supports the first detection element 11E.

The first detection part 10A has the first area S1 of the first detection element 11E, the first connection part length LC1 of the first connection part 31C, the first connection part width w1 of the first connection part 31C, and the first connection part width w1 of the first connection part 31C, the first connection part thickness t1 of the first connection part 31C, the first connection part material of the first connection part 31C, and the first distance d1. The first distance d1 is the distance between the first base region 41*a* and the first detection element 11E.

The second detection part 10B further includes the second support part 32S and the second connection part 32C. The second support part 32S is fixed to the base 41. The second connection part 32C is supported by the second support part 32S. The second connection part 32C supports the second detection element 12E.

The second detection part 10B has at least one of the second area S2 different from the first area S1 of the second detection element 12E, the second connection part length LC2 different from the first connection part length LC1 of the second connection part 32C, the second connection part width w2 different from the first connection part width w1 of the second connection part 32C, the second connection part thickness t2 different from the first connection part thickness t1 of the second connection part 32C, and the second connection part material different from the first connection part material of the second connection part 32C, or the second distance d2 different from the first distance d1. The second distance d2 is the distance between the second base region 41*b* and the second detection element 12E.

The third detection element 13E includes the third resistance member 13, the third other resistance member 13*a* and the third conductive member 23. The third conductive member 23 is between the third resistance member 13 and the third other resistance member 13*a*. With such a configuration, the concentration of the first output gas 81*a* can be detected more accurately.

The gas converter 80 can convert at least a part of the input gas 80M including the first substance 80*a* into the first output gas 81*a*.

In one example, the input gas 80M further includes the second substance 80*b*. The first substance 80*a* includes carbon dioxide. The second substance 80*b* includes hydrogen. In this case, the first output gas 81*a* includes at least one selected from the group consisting of methane and water.

In the embodiment, the first output gas 81*a* may pass through the first concentration sensor 51*c* after passing through the first flow rate sensor 51*f*.

The gas conversion system 310 may further include the gas converter controller 75. The gas converter controller 75 can control the gas converter 80 based on at least one of the first concentration value Vc1 or the first flow rate value Vf1 derived by the processor 71.

The gas conversion system 311 (see FIG. 2) may further include the second concentration sensor 52*c* and the second flow rate sensor 52*f*. The second output gas 81*b* is further output from the gas converter 80. The second concentration sensor 52*c* can detect the second concentration CN2 of the second target substance 81*bm* included in the second output gas 81*b*. The second flow rate sensor 52*f* can detect the second flow rate FL2 of the second output gas 81*b*.

The acquisitor 72 can further acquire the second concentration signal sc2 obtained from the second concentration sensor 52*c* and the second flow rate signal sf2 obtained from the second flow rate sensor 52*f*. The processor 71 can derive the second concentration value Vc2 corresponding to the second concentration CN2 based on the second concentration signal sc2. The processor 71 can derive the second corrected conversion coefficient k2' obtained by correcting the second conversion coefficient k2 based on the second concentration value Vc2, the second conversion coefficient k2 regarding the relationship between the second flow rate signal sf2 and the second flow rate FL2. The processor 71 can derive the second flow rate value Vf2 corresponding to the second flow rate FL2 based on the second flow rate signal sf2 using the second corrected conversion coefficient k2'.

Embodiments may include the following configurations (e.g. technical proposals).

Configuration 1

A data processing device, comprising:

an acquisitor configured to acquire a first concentration signal obtained from a first concentration sensor configured to detect a first concentration of a first target substance included in a first output gas and a first flow rate signal obtained from a first flow rate sensor con figured to detect a first flow rate of the first output gas; and a processor, the processor being configured to derive a first concentration value corresponding to the first concentration based on the first concentration signal, the processor being configured to derive a first corrected conversion coefficient obtained by correcting a first conversion coefficient relating to a relationship between the first flow rate signal and the first flow rate based on the first concentration value, and the processor being configured to derive a first flow rate value corresponding to the first flow rate based on the first flow rate signal using the first corrected conversion coefficient.

Configuration 2

The data processing device according to Configuration 1, wherein an absolute value of a difference between a time at which the acquisitor obtains the first concentration signal from the first concentration sensor and a time at which the acquisitor obtains the first flow rate signal from the first flow rate sensor is 10 seconds or less.

Configuration 3

The data processing device according to Configuration 1 or 2, wherein at least a part of the first concentration sensor includes a MEMS structure.

Configuration 4

The data processing device according to any one of Configurations 1 to 3, wherein the first output gas is output from a gas converter, and the gas converter is configured to convert at least a part of an input gas including a first substance into the first output gas.

Configuration 5

The data processing device according to Configuration 4, wherein the input gas further includes a second substance, the first substance includes carbon dioxide, and the second substance includes hydrogen.

Configuration 6

The data processing device according to Configuration 5, wherein the first output gas includes at least one selected from a group consisting of methane, water, carbon dioxide, and hydrogen.

Configuration 7

The data processing device according to any one of Configurations 1 to 3, wherein the acquisitor is configured to further acquire a second concentration signal obtained from a second concentration sensor configured to detect a second concentration of a second target substance included in a second output gas and a second flow rate signal obtained from a second flow rate sensor configured to detect a second flow rate of the second output gas, the processor is configured to derive a second concentration value corresponding to the second concentration based on the second concentration signal, the processor is configured to derive a second corrected conversion coefficient obtained by correcting a second conversion coefficient regarding a relationship between the second flow rate signal and the second flow rate based on the second concentration value, and the processor is configured to derive a second flow rate value corresponding to the second flow rate based on the second flow rate signal using the second corrected conversion coefficient.

Configuration 8

The data processing device according to Configuration 7, wherein an absolute value of a difference between a time at which the acquisitor obtains the second concentration signal from the second concentration sensor and a time at which the acquisitor obtains the second flow rate signal from the second flow rate sensor is 10 seconds or less.

Configuration 9

The data processing device according to Configuration 7 or 8, wherein at least a part of the second concentration sensor includes a MEMS structure.

Configuration 10

The data processing device according to any one of Configurations 7 to 9, wherein the second output gas is output from a gas converter, and the gas converter is configured to convert at least a part of an input gas including a first substance into the first output gas and the second output gas.

Configuration 11

The data processing device according to Configuration 10, wherein the gas converter generates the first output gas and the second output gas from the first substance using electrolytic solution, and the first substance includes carbon dioxide.

Configuration 12

The data processing device according to Configuration 11, wherein the first output gas includes at least one selected from a group consisting of carbon monoxide, hydrogen, water, and carbon dioxide, and the second output gas includes at least one selected from a group consisting of carbon dioxide, oxygen, water, and hydrogen.

Configuration 13

A gas conversion system, comprising:

the data processing device according to any one of Configurations 1 to 6;

the first concentration sensor;

the first flow rate sensor; and a gas converter, the first output gas being output from the gas converter, the first concentration sensor including a first detection part including a first detection element, a second detection part including a second detection element, a third detection part including a third detection element, and a base, the base including a first base region, a second base region, and a third base region, a first gap being provided between the first base region and the first detection element, a second gap being provided between the second base region and the second detection element, and a third gap being provided between the third base region and the third detection element.

Configuration 14

The gas conversion system according to Configuration 13, wherein the first detection part further includes a first support part and a first connection part, the first support part is fixed to the base, the first connection part is supported by the first support part, the first connection part supports the first detection element, the first detection part has a first area of the first detection element, a first connection part length of the first connection part, a first connection part width of the first connection part, a first connection part thickness of the first connection part, a first connection part material of the first connection part, and a first distance, the first distance is a distance between the first base region and the first detection element, the second detection part further includes a second support part and a second connection part, the second support part is fixed to the base, the second connection part is supported by the second support part, the second connection part supports the second detection element, the second detection part includes at least one of a second area different from the first area of the second detection element, a second connection part length different from the first connection part length of the second connection part, a second connection part width different from the first connection part width of the second connection part, a second connection part thickness different from the first connection part thickness of the second connection part, a second connection part material different from the first connection part material of the second connection part, or a second distance different from the first distance, the second distance is a distance between the second base region and the second detection element, the third detection element includes a third resistance member, a third other resistance member, and a third conductive member, and the third conductive member is between the third resistance member and the third other resistance member.

Configuration 15

The gas conversion system according to Configuration 13 or 14, wherein the gas converter is configured to convert at least a part of an input gas including a first substance into the first output gas.

Configuration 16

The gas conversion system according to Configuration 15, wherein the input gas further includes a second substance, the first substance includes carbon dioxide, and the second substance includes hydrogen.

Configuration 17

The gas conversion system according to Configuration 16, wherein the first output gas includes at least one selected from a group consisting of methane, water, carbon dioxide, and hydrogen.

Configuration 18

The gas conversion system according to any one of Configurations 13 to 17, wherein the first output gas passes through the first concentration sensor after passing through the first flow rate sensor.

Configuration 19

The gas conversion system according to any one of Configurations 13 to 18, further comprising:

a gas converter controller, the gas converter controller being configured to control the gas converter based on at least one of the first concentration value or the first flow rate value derived from the processor.

Configuration 20

The gas conversion system according to any one of Configurations 13 to 19, further comprising:

a second concentration sensor and a second flow rate sensor, a second output gas being further output from the gas converter, the second concentration sensor being configured to detect a second concentration of a second target substance included in the second output gas, the second flow rate sensor being configured to detect a second flow rate of the second output gas, the acquisitor being configured to further acquire a second concentration signal obtained from the second concentration sensor and a second flow rate signal obtained from the second flow rate sensor, the processor being configured to derive a second concentration value corresponding to the second concentration based on the second concentration signal, the processor being configured to derive a second corrected conversion coefficient obtained by correcting a second conversion coefficient regarding a relationship between the second flow rate signal and the second flow rate based on the second concentration value, and the processor being configured to derive a second flow rate value corresponding to the second flow rate based on the second flow rate signal using the second corrected conversion coefficient.

According to the embodiments, it is possible to provide a data processing device and a gas conversion system capable of improving characteristics.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in gas conversion systems such as bases, detection parts, processors, gas converters, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all data processing devices, and gas conversion systems practicable by an appropriate design modification by one skilled in the art based on the data processing devices, and the gas conversion systems described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A gas conversion system, comprising:
a gas converter configured to convert at least a part of an input gas into a first output gas, and output the first output gas;
a first concentration sensor configured to detect a first concentration of a first target substance included in the first output gas and output a first concentration signal;
a first flow rate sensor configured to detect a first flow rate of the first output gas and output a first flow rate signal;
a data processing device; and
a gas converter controller,
the first concentration sensor including a first detection part including a first detection element, a second detection part including a second detection element, a third detection part including a third detection element, and a base,
the base including a first base region, a second base region, and a third base region,
a first gap being provided between the first base region and the first detection element,
a second gap being provided between the second base region and the second detection element, and
a third gap being provided between the third base region and the third detection element,
wherein the data processing device comprises a processor configured to:
acquire the first concentration signal from the first concentration sensor and the first flow rate signal from the first flow rate sensor;
derive a first concentration value corresponding to the first concentration based on the first concentration signal;
derive a first corrected conversion coefficient obtained by correcting a first conversion coefficient relating to a relationship between the first flow rate signal and the first flow rate based on the first concentration value; and
derive a first flow rate value corresponding to the first flow rate based on the first flow rate signal using the first corrected conversion coefficient, and
wherein the gas converter controller is configured to control the gas converter based on at least one of the first concentration value or the first flow rate value derived from the processor.

2. The system according to claim 1, wherein
the first detection part further includes a first support part and a first connection part,
the first support part is fixed to the base,
the first connection part is supported by the first support part,
the first connection part supports the first detection element,
the first detection part has a first area of the first detection element, a first connection part length of the first connection part, a first connection part width of the first connection part, a first connection part thickness of the first connection part, a first connection part material of the first connection part, and a first distance, the first distance is a distance between the first base region and the first detection element,
the second detection part further includes a second support part and a second connection part,
the second support part is fixed to the base,
the second connection part is supported by the second support part,
the second connection part supports the second detection element,
the second detection part includes at least one of a second area different from the first area of the second detection element, a second connection part length different from the first connection part length of the second connection part, a second connection part width different from the first connection part width of the second connection part, a second connection part thickness different from the first connection part thickness of the second connection part, a second connection part material different from the first connection part material of the second connection part, or a second distance different from the first distance, the second distance is a distance between the second base region and the second detection element,
the third detection element includes a third resistance member, a third other resistance member, and a third conductive member, and
the third conductive member is between the third resistance member and the third other resistance member.

3. The system according to claim 1, wherein
the input gas includes a first substance.

4. The system according to claim 3, wherein
the input gas further includes a second substance,
the first substance includes carbon dioxide, and
the second substance includes hydrogen.

5. The system according to claim 4, wherein
the first output gas includes at least one selected from a group consisting of methane, water, carbon dioxide, and hydrogen.

6. The system according to claim 1, wherein
the first output gas passes through the first concentration sensor after passing through the first flow rate sensor.

7. The system according to claim 1, further comprising:
a second concentration sensor and a second flow rate sensor,
a second output gas being further output from the gas converter,
the second concentration sensor being configured to detect a second concentration of a second target substance included in the second output gas,
the second flow rate sensor being configured to detect a second flow rate of the second output gas,
the processor being configured to further acquire a second concentration signal obtained from the second concentration sensor and a second flow rate signal obtained from the second flow rate sensor,
the processor being configured to derive a second concentration value corresponding to the second concentration based on the second concentration signal,
the processor being configured to derive a second corrected conversion coefficient obtained by correcting a second conversion coefficient regarding a relationship between the second flow rate signal and the second flow rate based on the second concentration value, and
the processor being configured to derive a second flow rate value corresponding to the second flow rate based on the second flow rate signal using the second corrected conversion coefficient.

* * * * *